United States Patent
Merlo

(10) Patent No.: US 6,217,249 B1
(45) Date of Patent: Apr. 17, 2001

(54) JOINT MECHANISMS AND CONNECTOR

(76) Inventor: Werner O. Merlo, 51203 Range Rd. 265, Spruce Grove, Alberta (CA), T7Y 1E7

( * ) Notice: Subject to any disclaimer, the term of this patent is extended or adjusted under 35 U.S.C. 154(b) by 0 days.

(21) Appl. No.: 09/160,176

(22) Filed: Sep. 25, 1998

(51) Int. Cl.$^7$ .................. F16C 11/06; F16D 1/12
(52) U.S. Cl. ............ 403/90; 403/321; 403/128; 403/131
(58) Field of Search ............... 403/322.1, 325, 403/321, 327, 128, 131, 164, 165, 90

(56) References Cited

U.S. PATENT DOCUMENTS

| | | | |
|---|---|---|---|
| 282,551 | * 8/1883 | McLean | 89/9 X |
| 2,859,059 | * 11/1958 | Loach et al. | 403/103 |
| 3,433,510 | * 3/1969 | Hulterstrum | 403/90 X |
| 3,535,976 | * 10/1970 | Osuga | 84/421 X |
| 3,691,788 | 9/1972 | Mazziotti . | |
| 3,841,769 | * 10/1974 | Bowerman | 403/90 |
| 4,433,854 | * 2/1984 | Smith | 403/131 X |
| 4,597,599 | * 7/1986 | Bisbing | 292/174 |
| 4,620,813 | 11/1986 | Lacher . | |
| 4,824,278 | 4/1989 | Chang . | |
| 4,863,201 | * 9/1989 | Carstens | 285/317 |
| 4,938,496 | * 7/1990 | Thomas et al. | 403/324 X |
| 4,974,802 | * 12/1990 | Hendren | 403/90 X |
| 5,092,898 | * 3/1992 | Bekki et al. | 623/22 X |
| 5,265,969 | 11/1993 | Chuang . | |
| 5,280,871 | * 1/1994 | Chuang | 403/90 X |
| 5,472,254 | * 12/1995 | Wander | 403/321 X |
| 5,588,767 | * 12/1996 | Merlo | 403/128 |
| 6,059,480 | * 5/2000 | Maughan et al. | 403/131 |

FOREIGN PATENT DOCUMENTS

| | | | |
|---|---|---|---|
| 143314 | * 11/1930 | (CH) | 403/327 |
| 339415 | * 7/1921 | (DE) | 403/90 |
| 743641 | * 11/1943 | (DE) | 403/90 |
| 84 23 446 U | * 1/1986 | (DE) . | |
| 430069 | 11/1990 | (EP) . | |
| 472995 | * 12/1913 | (FR) | 403/328 |
| 462510 | * 1/1914 | (FR) | 403/328 |
| 635561 | * 3/1928 | (FR) | 403/90 |

* cited by examiner

Primary Examiner—Lynne H. Browne
Assistant Examiner—Ernesto Garcia
(74) Attorney, Agent, or Firm—Terry M Gernstein

(57) ABSTRACT

A joint mechanism and connector includes a rounded member having at least one concavity and which is connected to a first part, at least one actuator having a tip that is received in the concavity to lock a second part connected to the actuator to the first part. The rounded member has a recess defined thereon which receives spherical members on the rounded member. The actuator tip is received in concavities defined by the spherical members.

9 Claims, 16 Drawing Sheets

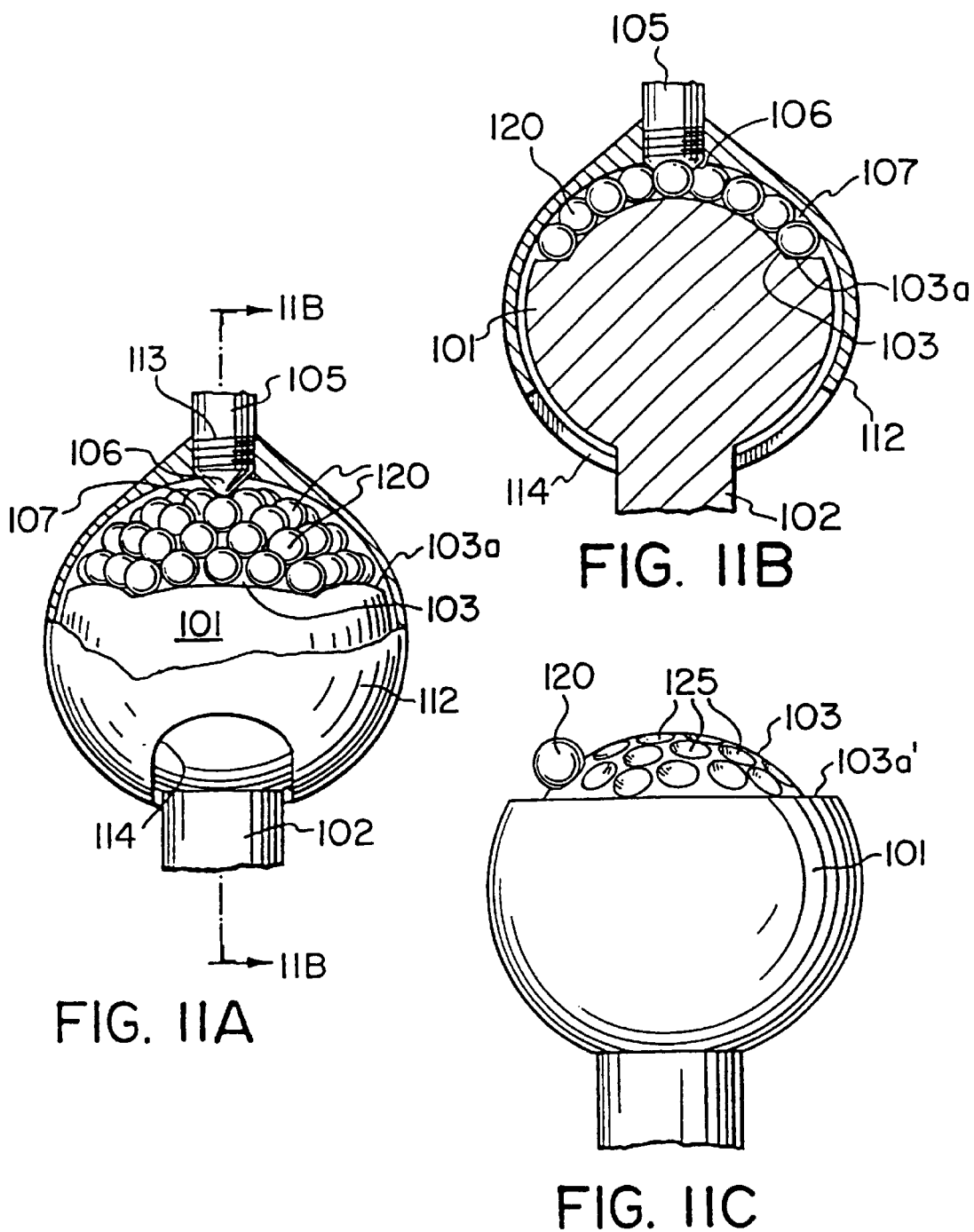

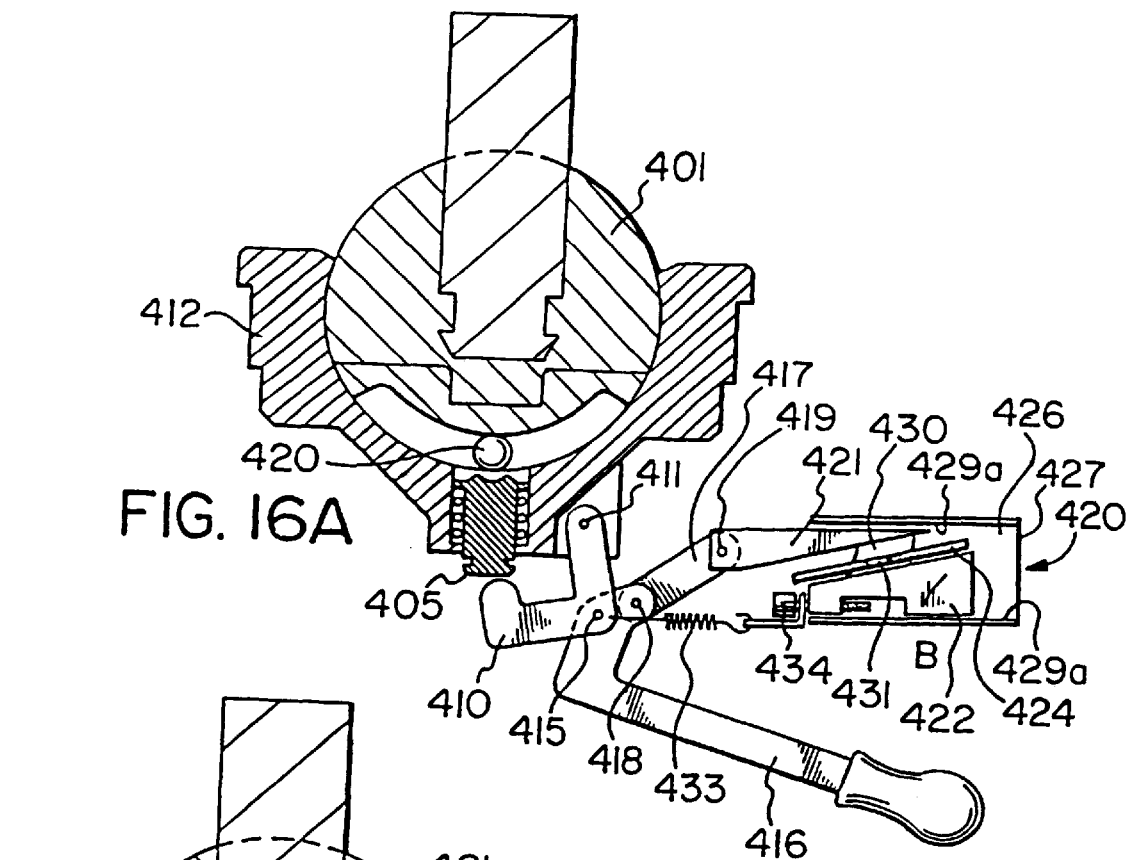
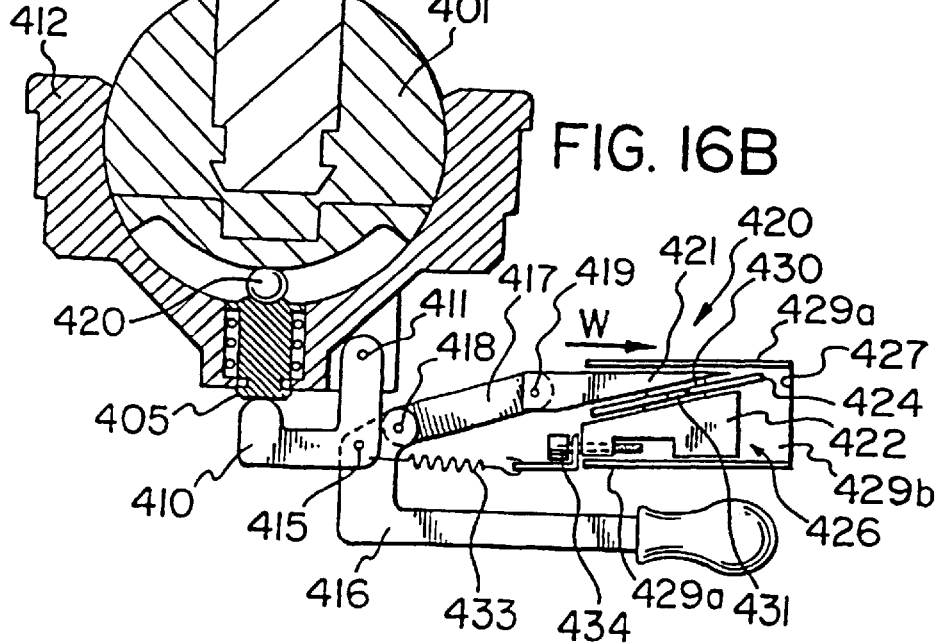

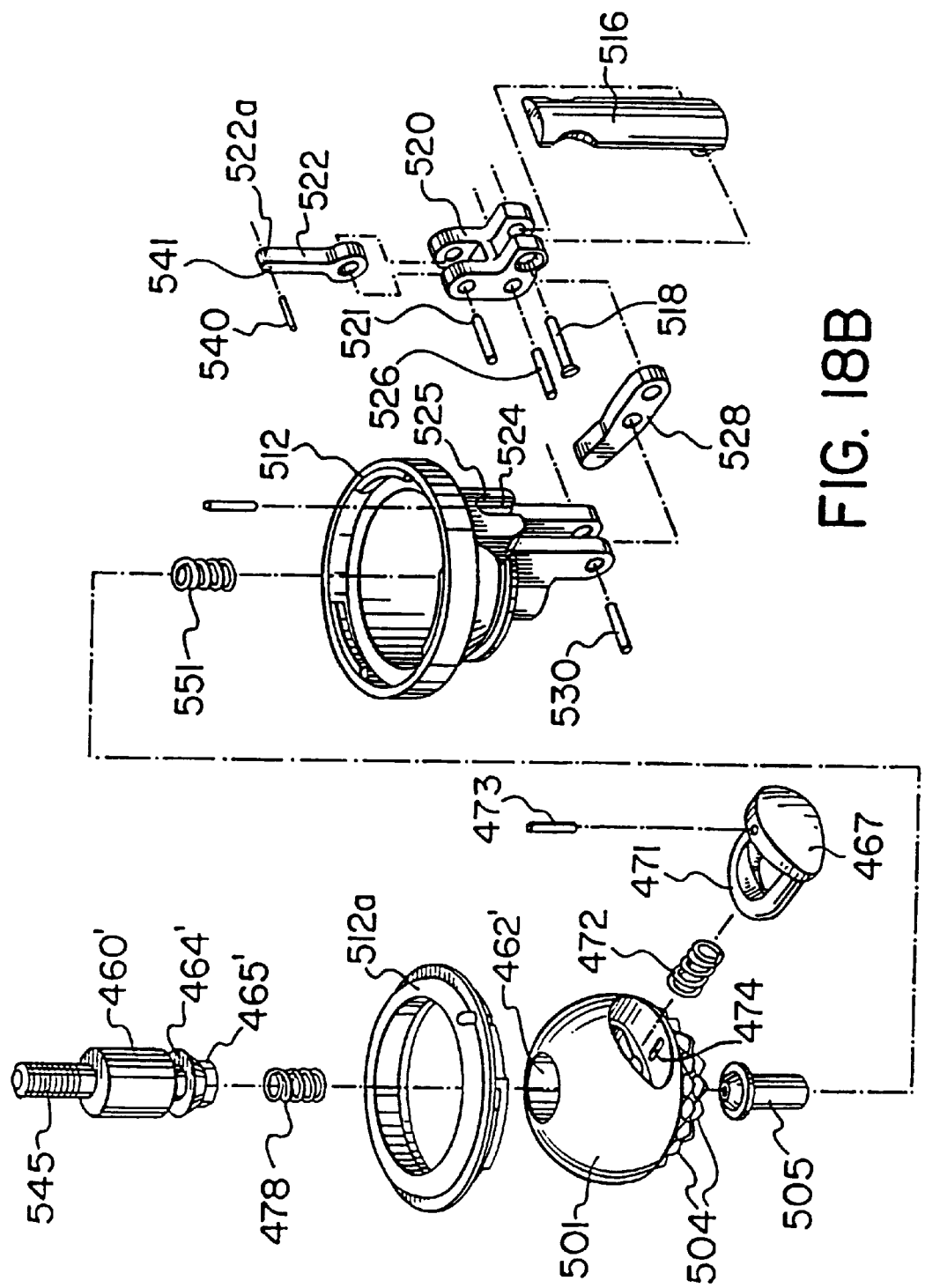

JOINT MECHANISMS AND CONNECTOR

FIELD OF THE INVENTION

The invention is directed to a joint and in particular, an angularly adjustable, releasably lockable joint mechanism for rigidly joining first and second parts at a selected orientation and apparatus for operating such a joint.

BACKGROUND OF THE INVENTION

Ball Joint

A ball joint mechanism includes generally a ball within a housing. Often the ball has attached thereto a rod which extends out beyond the housing. An actuator acts between the housing and the ball to fix the position of the ball, and therefore the angle of the rod, relative to the housing. A ball joint mechanism is disclosed, for example, in U.S. Pat. No. 5,280,871 where a plurality of holes are orderly and equally spaced apart in the surface of the ball for accepting the functional end of an actuator pin. A dimpled ball and an actuator having a spherical tip are also shown in U.S. Pat. No. 3,433,510. U.S. Pat. Nos. 3,841,769 and 4,620,813 show a socket having protuberances and a ball having dimples or indentations which engage to fix the orientation of rods attached thereto. U.S. Pat. No. 3,691,788 shows a ball having a grooved surface and an actuator having a spherical tip which locks up by engaging a groove. U.S. Pat. No. 892,105 shows a ball and socket whose surfaces are both knurled.

Angularly adjustable, releasably lockable ball joints are commonly used as part of an umbrella assembly, to lock a suspended canopy locked at a selected angle. Assemblies of this type are shown in U.S. Pat. Nos. 4,674,523 and 5,002,081. The frictional engagement of a ball and a socket, as well as a dimpled ball and spherical pin actuator, have been found to be insufficient when subjected to high torsional forces.

Prosthetic Terminal Device Locking Assembly

Terminal devices, such as artificial hands, swimming paddles, etc., are used in association with prosthetic limbs. Such terminal devices are attached by locking assemblies to the prosthetic limb. Known terminal device locking assemblies are difficult to operate, especially by persons who have only one hand.

A typical locking assembly includes a bore formed in the prosthetic limb which accepts and locks an adapted stem on the terminal device. The locking mechanism includes a button that must be actuated both to release the stem from the bore and to insert the stem into the bore. It will be appreciated that the operation of insertion is very difficult since it requires that the stem of the terminal device be inserted into the bore while actuating the button. The insertion operation is further complicated in some prior art embodiments having a stem, the end of which is shaped and must be aligned during the insertion operation with a mating shaped portion within the bore. Such stem/socket mating prevents undesirable rotation of the terminal device but complicates the insertion procedure.

SUMMARY OF THE INVENTION

A ball joint mechanism has been invented which is particularly adapted for use with angularly adjustable, locking parts which are subject to high torsional forces.

In accordance with a broad aspect of the present invention there is provided an angularly adjustable, releasably lockable joint mechanism for rigidly joining first and second parts at a selected orientation, said mechanism comprising a rounded member secured to the first part and a socket secured to the second part, the rounded member being adapted to be rotatable within the socket, and a disengageable actuator acting between the rounded member and the socket, having a tip and means being operative to advance the tip to lock up by penetrating a concavity disposed on one of the rounded member or the socket and to retract the tip to remove it from the concavity, said actuator being connected to lock the positioning of the socket relative to the rounded member when penetrating the concavity, the concavity being formed by a spaced arrangement of engaging surfaces; the spaced arrangement having a polygonal configuration; and the engaging surfaces, actuator tip and spaced arrangement being dimensioned so that the tip can penetrate the concavity of the spaced arrangement and contact all of the engaging surfaces of the arrangement that it penetrates, whereby the tip and the arrangement of engaging surfaces lock together.

In accordance with a broad aspect of the present invention there is provided an angularly adjustable, releasably lockable joint mechanism for rigidly joining first and second parts at a selected orientation, said mechanism comprising a rounded member having a plurality of concavities in association therewith and being secured to the first part, a disengageable actuator having a tip and being operative to advance the tip to lock up with the rounded member by penetrating at least one concavity or to retract the tip to disengage it from the rounded member, said actuator being connected with the second part, and means for holding the first part, the second part, the rounded member and the actuator together, said means being operative to allow the first part and the second part to change relative orientation when the actuator tip is retracted, each concavity being formed by a spaced arrangement of engaging surfaces; the spaced arrangement having a polygonal configuration; and the engaging surfaces, actuator tip and spaced arrangement being dimensioned so that the tip can penetrate the concavity of each spaced arrangement and contact all of the engaging surfaces of the arrangement that it penetrates, whereby the tip, the arrangement of engaging surfaces and the rounded member lock together.

The rounded member can be formed in any suitable way to be rotatable within the socket, for example, the rounded member can be spherical, or have substantially spherical portions or be cylindrical in shapes. The first member is formed to be suitable to support the engaging surfaces.

The engaging surfaces can be in fixed position on the rounded member. As an example, the engaging surfaces can be protuberances formed integrally with the rounded member or separate therefrom and mounted on the rounded member. The protuberances which are mounted onto the rounded member can be in the form of, for example, a pin or ball bearing. In another embodiment, the engaging surfaces are members fixed in position on the surface of the rounded member but formed separately from the rounded member and not secured thereto. For example, in one such embodiment the engaging surfaces are formed by closely packed spherical members, for example ball bearings, maintained in position on the surface of the rounded member by limiting means such as depressions, recessed areas or ridges formed on the surface of the rounded member to limit the movement of the ball bearings over the surface of the rounded member. The ball bearings are maintained about the rounded member by a shell or housing.

By arranging the engaging surfaces in accordance with a regular polygonal configuration, the longitude and latitude of the concavity sites on a rounded member can be mathematically definable and the concavity sites can be regularly spaced from one another. The polygonal configuration can be, for example, a triangle, a square, polygons having greater than four sides or combinations thereof. The use of a triangular pattern yields the largest number of concavity sites on a rounded member that is spherical.

In accordance with another broad aspect of the present invention, there is provided an angularly adjustable, releasable lockable joint mechanism for rigidly joining first and second parts at a selected orientation, said mechanism comprising a first member secured to the first part and a shell secured to the second part, the first member being adapted to be rotatable about a single axis within the shell and a disengageable actuator acting between the first member and the shell, having at least one tip and means being operative to advance the tip to lock up with the first member by penetrating at least one concavity disposed on the first member and to retract the tip to remove it from the concavity, said actuator being connected to lock the positioning of the shell relative to the first member when penetrating the concavity, the concavity being elongate and formed substantially parallel to the axis of rotation. In one embodiment, the first member includes two generally semi-spherical halves joined by a narrow band having a surface formed with elongate concavities extending between the semi-spherical halves. An alternate arrangement includes a gear-like structure contained in a suitable shell and locked by an actuator.

According to the invention, the penetrating tip of the actuator contacts the surfaces of the engaging surfaces defining the penetrated concavity. In contacting the engaging surfaces defining the concavity, the actuator tip can also touch the bottom of the concavity. To enhance locking between the actuator tip and the engaging surfaces, it is preferred that the actuator tip remains spaced from the bottom of the concavity at full penetration. Where the engaging surfaces are protuberances in fixed position on the rounded member, after extended use of the joint the protuberances may show significant wear allowing the actuator tip to touch the bottom of the concavity without properly engaging the protuberances. To prevent such incomplete locking, a depression can be formed in the surface of the rounded member at each concavity to increase the depth of the concavity between the protuberances.

The actuator, useful in joints according to the present invention, can have multiple tips disposed to penetrate simultaneously more than one concavity. Furthermore, the actuator or its tip can have a floating seating to enable self-adjustment. The actuator tip can be rounded or, preferably, faceted to reduce axial rotation of the actuator within the concavity. Another actuator tip useful in the present invention is rounded with protuberances formed thereon to enhance engagement with the engaging surfaces. A further actuator tip useful in the present invention is formed of resilient material.

In a preferred embodiment, the actuator is biased, such as by spring loading, such that it is prevented from fully falling out of contact with the engaging surfaces when the actuator is not in the locking position. Thus, the actuator tip is free to ride over the engaging surfaces while not locked in position. This is particularly useful to prevent jamming of the joint, where the engaging surfaces are members which are not secured to the surface of the rounded member.

In one embodiment, the spherical members are maintained in a cavity formed in the socket surrounding the rounded member. The spherical members and rounded member can be formed of a material which is magnetizable so that the spherical members are held by a magnetic attraction about the rounded member. This is of particular use in assembly and disassembly. In one embodiment, the spherical members are disposed over the entire surface of the rounded member. In another embodiment, the spherical members are disposed over a selected region of the rounded member. The inner surface of the socket and/or the outer surface of the rounded member can be knurled, indented, or roughened to enhance the engagement between the rounded member, spherical members and socket.

The actuator, useful in the present invention, can be driven by any suitable means. The switch mechanism is preferably adjustable to select the locking tension. The switch mechanism is preferably manually or automatically adjustable to accommodate locking at any concavity depth. The mechanism can be adjustable to select the distance the actuator will extend into the socket when fully inserted, adjustable to lock when the actuator is extending any distance into the socket and/or be adjustable to lock when the actuator comes into contact with an engaging surface.

The joint mechanism according to the invention finds application in different fields. In addition to its use in connection with sun shade umbrellas, the joint is also useful in prosthetic or orthotic joints or in other angularly adjustable apparatus, such as wheel chair head rests and mirror mounts.

For use in the field of prosthetics, a joint can have optionally an actuator which is controlled by a switch mechanism or drive means which can be actuated through the rubber sheath of an artificial limb, without having a lever extending through the sheath and without reaching up under the sheath.

The actuator useful in the present invention can be driven by any suitable means. The switch mechanism is preferably adjustable to select the locking tension. The switch mechanism is preferably manually or automatically adjustable to accommodate locking at any concavity depth. The mechanism can be adjustable to select the distance the actuator will extend into the socket when fully inserted, adjustable to lock when the actuator is extending any distance into the socket and/or be adjustable to lock when the actuator comes into contact with an engaging surface.

Thus, in accordance with a further broad aspect of the present invention there is provided an angularly adjustable, releasable lockable joint mechanism for rigidly joining first and second parts at a selected orientation, said mechanism comprising a rounded member having a plurality of concavities in association therewith and being secured to the first part, a disengageable actuator having a tip and means being operative to advance the tip to lock up with the rounded member by penetrating at least one concavity or to retract the tip to disengage it from the rounded member, said actuator being connected with the second part, and means for holding the parts, rounded member and actuator together, said means being operative to allow the parts to change relative orientation when the actuator tip is retracted, the actuator being driven by pushable means to advance and retract the tip.

Preferably the mechanism is mechanical and does not require the use of an electrical source. In one embodiment the mechanism includes a first part and a second part arranged to pivot about each other at their first ends between a raised position and a collapsed position and the first and second parts being positioned to drive the actuator advance the tip when the parts are in their raised position and being positioned to release the actuator to retract the tip when the parts are in their collapsed position and a button which upon activation by an operator drives the parts between their first and second position. Preferably, the button is sized to be actuated through the rubber sheath of an artificial limb.

A prosthetic terminal device locking assembly has been invented which facilitates exchange of terminal devices on a prosthetic limb. The locking assembly includes a stem formed on the terminal device or prosthetic limb and a bore formed in the other of the prosthetic limb or terminal device. Biased retaining means act between the stem and the bore to allow passage of the stem into the bore, when force is applied to the stem, and to engage between the stem and the bore, to prevent removal of the stem from the bore, once the stem has been inserted a selected distance into the bore. The stem is released from the bore by driving the biasing means out of engagement between the stem and the bore.

In accordance with a broad aspect of the present invention, there is provided a prosthetic terminal device locking assembly comprising: a stem formed on one of a prosthetic device or a terminal device; a bore formed in the other of the prosthetic device or a terminal device; a retaining member mounted to act between the stem and the bore and biased to allow insertion of the stem into the bore, when force is applied to drive the stem into the bore, and to engage between the stem and the bore when the stem is inserted a selected distance into the bore; and means for driving the retaining means out of engagement between the bore and the stem to allow removal of the stem from the bore.

The retaining member can be mounted in the bore or on the stem and preferably engages a groove or a flange formed on the other of the stem or the bore.

The means for driving the retaining means is preferably a simple device such as, for example, a lever or a button to which force can be applied. Preferably, the means is a button moveable along a single axis to release the lock, to thereby facilitate operation.

In accordance with another broad aspect of the present invention, there is provided a prosthetic terminal device locking assembly comprising a prosthetic device having a bore for accepting an adapted stem of a terminal device, the stem having a recess formed therein and a retaining member mounted in association with the bore, biased to extend into the bore, and adapted to be urged out of the bore by insertion of the stem into the bore, the retaining member being disposed along the bore to extend into the recess of the stem when the stem is inserted a selected distance into the bore.

Preferably, at least one of the stem and the retaining member are adapted, such as by chamfering or tapering of a leading edge, to facilitate movement of the retaining member out of the bore by insertion of the stem and application of force thereon. In a preferred embodiment, both the leading edge of the stem and the outwardly facing portion of the retaining member are chamfered.

Preferably, to prevent rotation of the terminal device within the bore, the bore and stem have portions with mating edges. Preferably, the stem and bore are formed in cross section as mating hexagons or squares. Preferably, the shaped portions are disposed such that they do not interfere with the locking operation.

To facilitate removal of the terminal device from the bore, a biasing means is preferably provided in the bore to bias the stem out of the bore, when the retaining means is removed from the groove of the stem.

BRIEF DESCRIPTION OF THE DRAWINGS

Further characteristics and advantages of the invention will become apparent from the detailed description of embodiments thereof, illustrated only by way of non-limitative examples in the accompanying drawings, wherein:

FIG. 11A a perspective, partly cut away view of a joint having a rounded member with a plurality of ball bearings disposed in a recessed area in the surface of the rounded member;

FIG. 11B is a sectional view along line 11B—11B of FIG. 11A;

FIG. 11C is a perspective view of an alternate rounded member useful in the joint of FIG. 11A;

FIG. 16A is a schematic view of another actuator drive mechanism useful in the present invention;

FIG. 16B is a view of the mechanism of FIG. 16A in the locked position;

FIG. 18B is an exploded view of the joint of FIG. 18A.

DETAILED DESCRIPTION OF THE PREFERRED EMBODIMENTS

Figure 1:
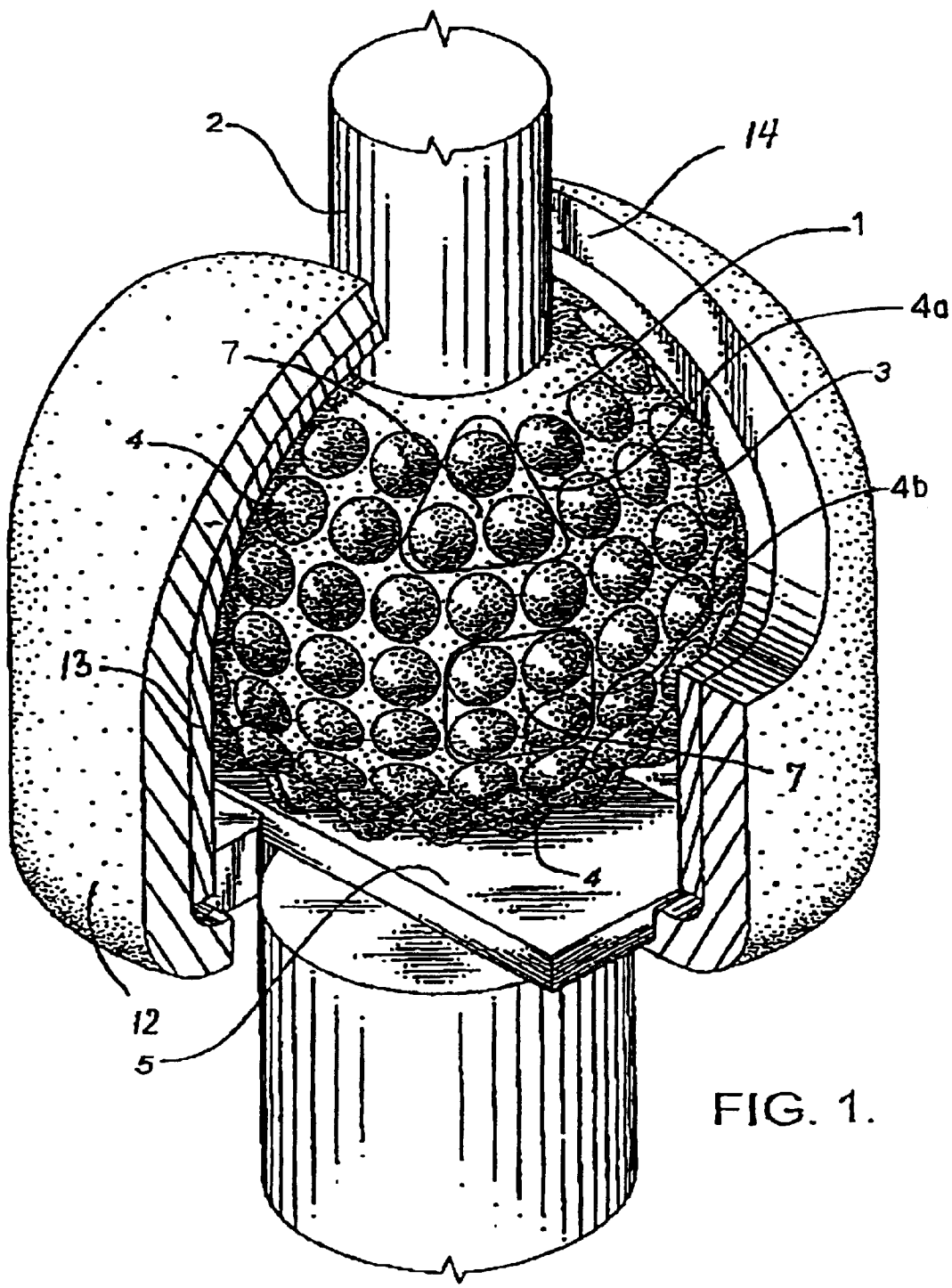
FIG. 1 is a perspective, partly cut away view showing a rounded member, an actuator and connection housing assembled.
Figure 2:
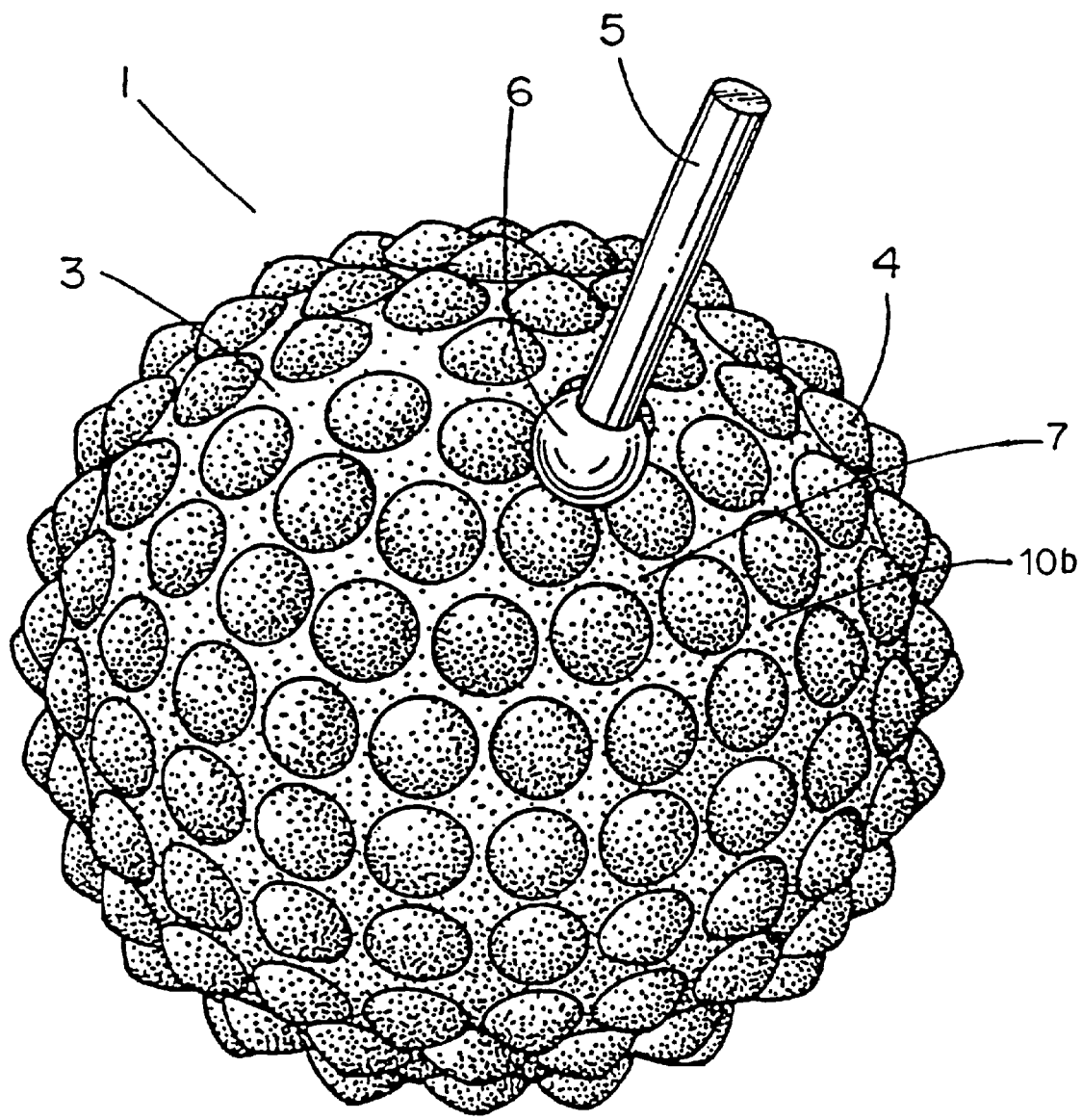
FIG. 2 is a perspective view showing a ball and pin-type actuator in simplified form.
Figure 3:
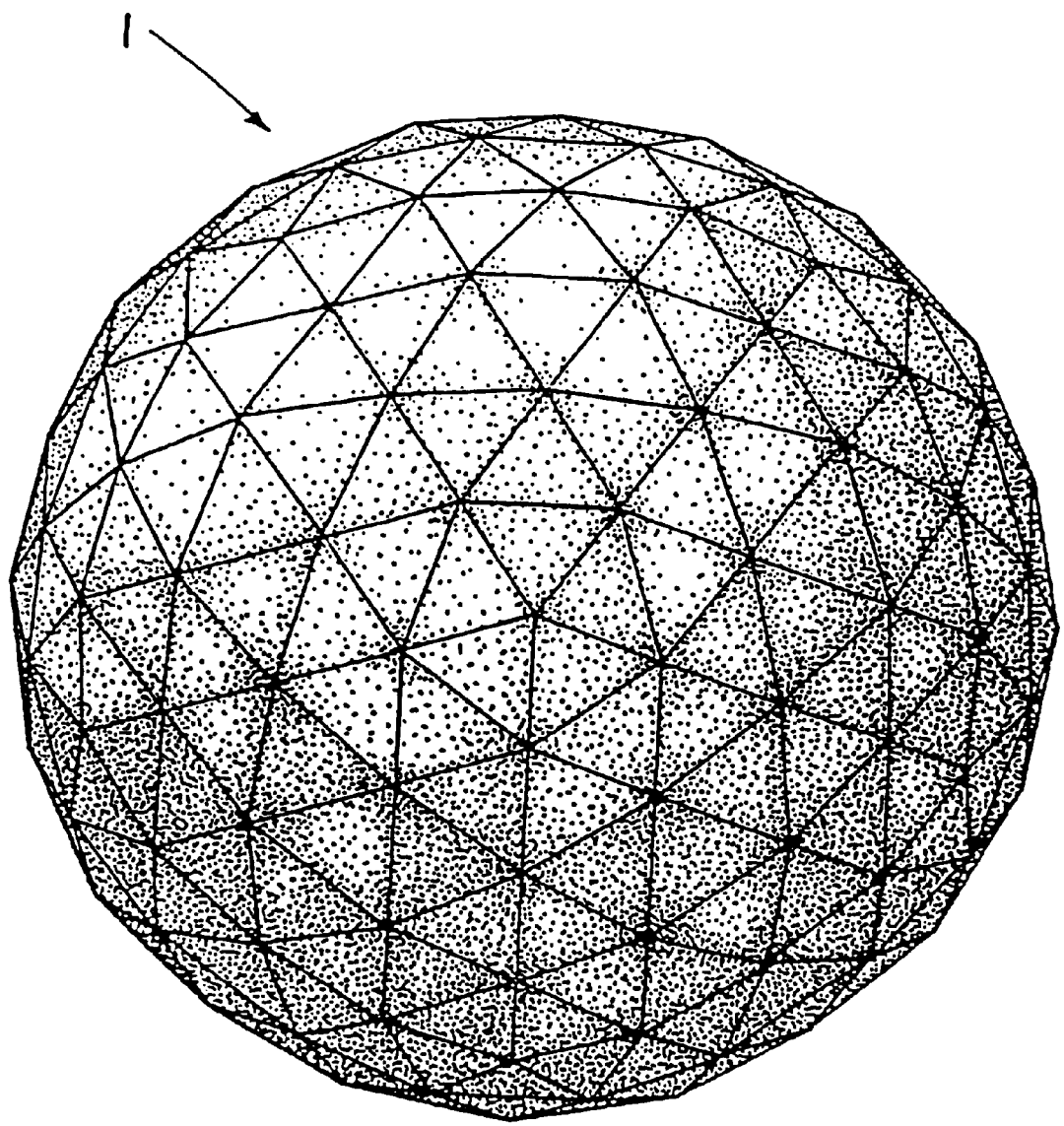
FIG. 3 is a side view of a ball having its surface divided into triangles to establish a pattern of protuberances.

With reference to FIG. 1, a joint mechanism according to the present invention includes a rounded member or ball 1 connected with a shank 2. The surface 3 of the ball 1 is formed with areas of triangular patterns 4a and square patterns 4b of engaging surfaces formed as protuberances 4. The spacing, area and size of the triangular patterns 4a is substantially consistent, and the same is true of the square patterns 4b. The size and spacing of each protuberance 4 in each pattern is substantially consistent. The patterns define concavities 7 between the protuberances.

The joint mechanism further comprises an actuator 5 shown having a rounded or spherical tip 6 (FIG. 2 and FIGS. 5 to 7). The tip can also be faceted, not shown, to reduce axial rotation thereof when locked in a concavity 7. The actuator 5 can be advanced or retracted, for example by a bolt (not shown), such that its tip 6 is inserted into or withdrawn from concavity 7 defined by pattern 4a, 4b of three or four protuberances 4. When inserted into a concavity rigidly so that it is in frictional engagement with the protuberances of the concavity, the actuator tip is locked with the ball.

Figure 5:
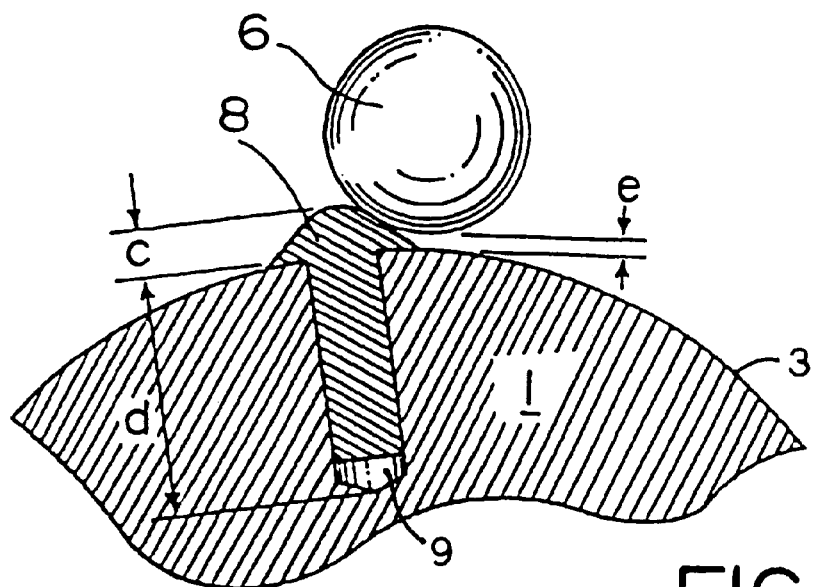
FIG. 5 is a schematic cross-section showing a pin having its shank positioned in a radial bore formed in the ball with its head defining a protuberance in contact with a spherical actuator end having a minimum clearance from the surface of the ball.
Figure 6:
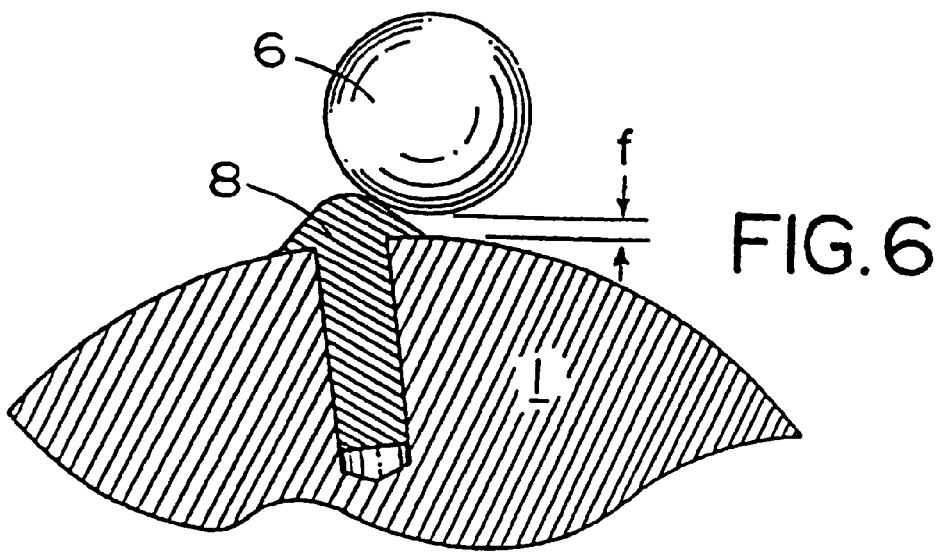
FIG. 6 is a cross-section according to FIG. 5 showing a maximum distance between actuator end and ball surface.
Figure 7:
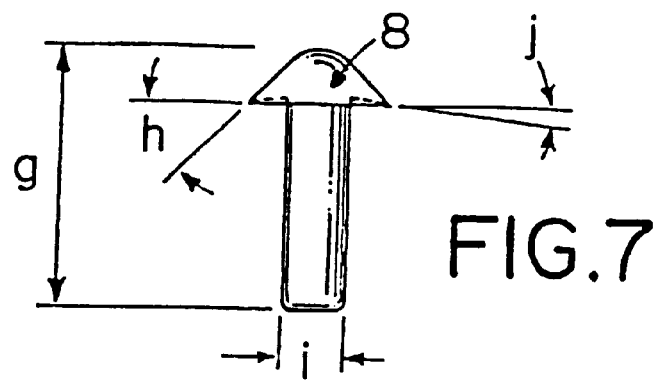
FIG. 7 is a side view of the pin according to FIGS. 5 and 6.
Figure 9:
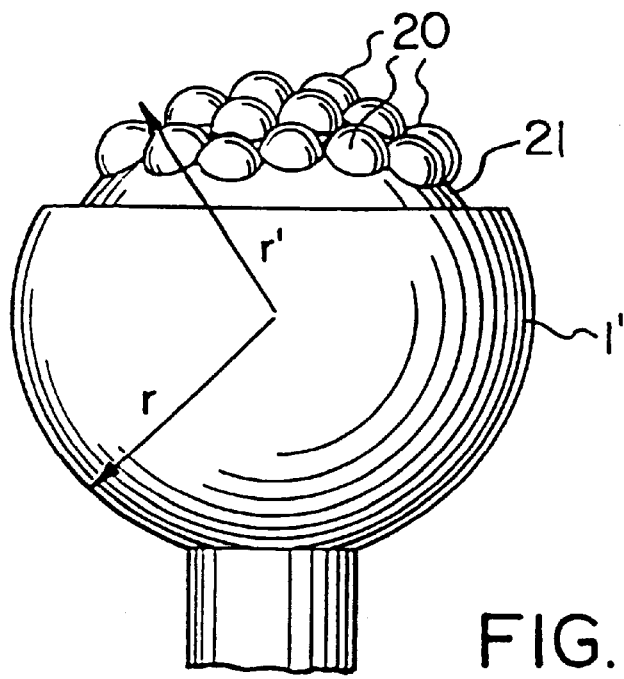
FIG. 9 is a side view of a ball having ball bearings in the surface thereof as engaging surfaces.

According to FIGS. 5 to 7, the protuberances 4 can be defined by the heads of pins 8 received and retained-in radial bores 9 formed in the ball 1. Alternately, as shown in FIG. 9, the protuberances could be defined by the exposed portion of ball bearings 20 embedded in the surface of ball 1.

To hold ball 1 and actuator 5 together and to allow these parts to change relative orientation when the actuator tip 6 is retracted, there is provided a rigid outer shell 12 (FIG. 1) and an inner shell liner 13 formed of a resilient material. In the outer shell 12 and inner shell 13 there is an opening 14. Shank 2 of ball 1 extends out through opening 14 which extends across the upper surface of said shells to thereby permit rotational movement of ball 1 within shells 12, 13.

Protuberances 4, actuator tip 6 and patterns 4a, 4b are dimensioned so that tip 6 can penetrate concavity 7 formed by each pattern 4a, 4b and contact all of the protuberances 4 of the pattern that it penetrates. Preferably, at full penetration tip 6 remains spaced from the surface 3 of ball 1. Referring to FIGS. 5 and 6:

c=radial height of protuberance 4 defined by the pin head d=radial length of bore 9 e=minimum clear distance between tip 6 and ball surface 3 f=maximum clear distance between tip 6 and ball surface 3 g=length of pin 8 plus its head h=slope angle of protuberance 4 i=diameter of pin 8 j=angle between bottom of the pin head and the tangent to ball surface 3.

An exemplary set of dimensions for the components of FIGS. 5 to 7 is provided in Table 1, for recommended maximum and minimum pin separation for an overall pattern of 162 pins.

TABLE 1

| Ball diameter: | 1.043" (26.5 mm) |
| --- | --- |
| pin diameter: | 0.142" (3.6 mm) |
| tip diameter: | 2.250" (6.4 mm) |

Dimensions:
c = 0.043" (1.1 mm)
d = 0.230" (5,8 mm)
e = 0.015" (0,4 mm)
f = 0.023" (0,6 mm)
g = 0.2360 (6 mm)
h = 43°
i = 0.063 (1,6 mm)
j = 6.0°

Figure 4:
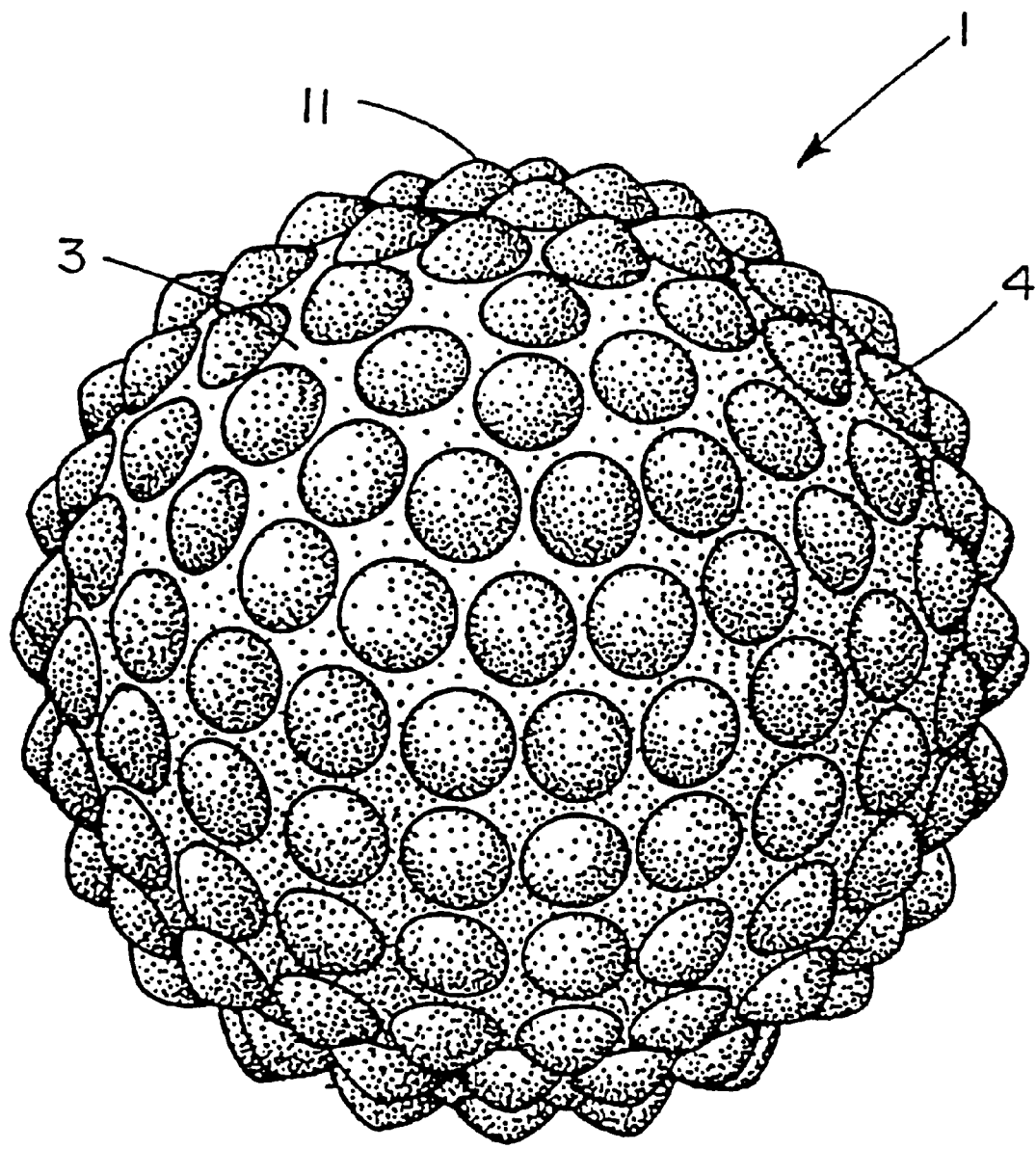
FIG. 4 is a side view of the ball of FIG. 3, with protuberances positioned at the apices of the triangles of FIG. 3.
Figure 8:
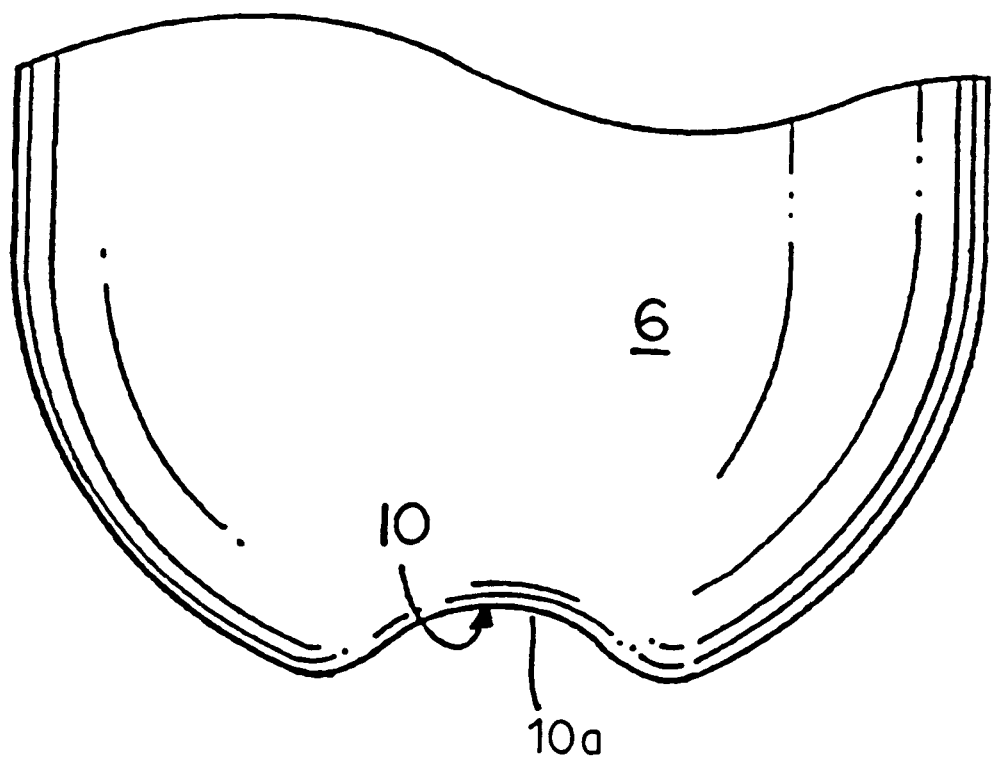
FIG. 8 is a cross-section of the rounded tip of an actuator having a central indentation in its end.

In an embodiment of the invention, the spherical tip 6 of the actuator 5 is formed to provide an indentation 10 in its end (FIG. 8). The indentation 10 may be configured to closely conform to the peak 11 (see FIG. 4) of each protuberance 4, so that if the tip 6 contacts directly a peak 11, the two parts will lock up. This adds as many locking positions as the number of protuberances 4 formed on the ball surface.

To create a firmer locking position, preferably, said peak 11 contacts the lateral area 10a of the penetrated indentation 10 and remains spaced from the bottom 10b of the indentation 10 at full penetration.

Referring to FIG. 9 another embodiment of a joint is shown herein, ball bearings 20 are embedded in the surface of the round member 1'. The ball can be used with a shell and actuator as shown in FIG. 1. The ball/ball bearing arrangement can be produced by any known process. As an example, the ball bearings, formed of stainless steel or the like, can be positioned in a mold with about half of their surface exposed in the mold and the material forming the ball, for example a polymer, can be injection molded about the ball bearings. The ball bearings can be disposed over the entire surface of the rounded member or over a selected portion of the rounded member, as shown, where a joint having preselected limitations as to its angular orientation is desired. In this embodiment it is preferred that the ball bearings are mounted in a recess 21 on the surface of the rounded member such that the radius r of the rounded member and the radius r' measured from the center of the rounded member to the outer limits of the mounted ball bearings are substantially equal. The permits a shell having a uniform inner radius to be used with the ball which facilitates shell manufacture. Preferably, the ball bearings are embedded in the ball in such a way as they are not free to drop out of position when the shell of the joint is removed from about the ball.

Figure 10:
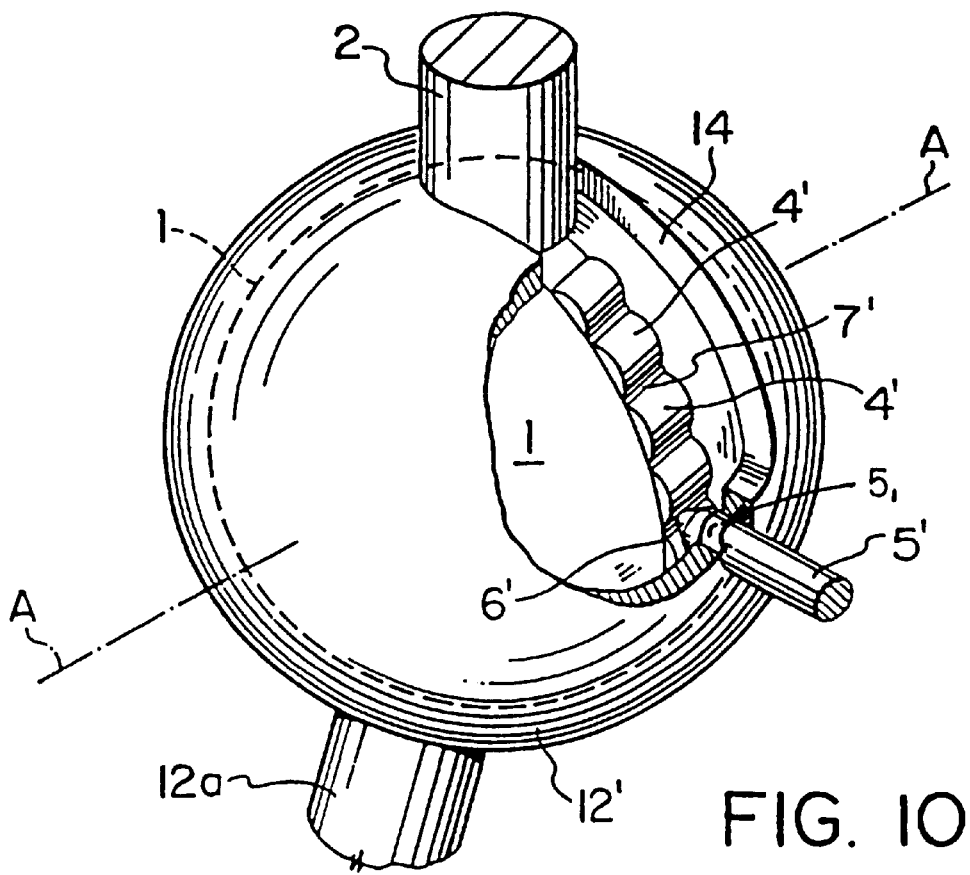
FIG. 10 is a perspective, partly cut away view showing another joint mechanism according to the present invention.

With reference to FIG. 10, another joint mechanism according to the present invention is formed to rotate about a single axis indicated at A. The joint includes a ball 1 connected to shank 2. The surface of the ball is formed with protuberances 4' which are elongate along an axis parallel to axis A. Between the protuberances are formed concavities 7' which also extend parallel to axis A. An actuator 5' having a rounded tip 6' is secured to a shell 12' and is moveable by screwing as by threads such as threads 5, to be advanced into or retracted from a concavity 7'.

An opening 14 is formed in shell 12' through which shank 2 extends. Shell 12' has attached thereto a second shank 12a which can be locked into a selected angular orientation relative to shank 2 by movement of ball 1 about axis A and locking into orientation by advancing actuator 5' to lock a concavity 7'.

In another embodiment, as shown in FIGS. 11A and 11B, the ball joint includes a rounded member 101 and a shank 102 attached thereto. A recessed area 103 on the surface of ball 101 accommodates an arrangement of ball bearings 120. The perimeter shape of the ball bearing arrangement is selected to be undulating and the edges 103a of area 103 conform closely to the perimeter shape of the arrangement of ball bearings to retain ball bearings 120 closely packed in position and to limit the movement of the ball bearings, relative to each other and over the surfaces of the rounded member.

The joint mechanism further includes an actuator 105 having a tip 106 shaped to enter one of the spaces 107 between adjacent ball bearings 120. A shell 112 engages actuator 105 at threaded area 113 and closely surrounds rounded member 101 and ball bearings 120. An opening 114 allows for extension of shank 102 from rounded member 101 and movement thereof relative to shell 112. The ball joint locks when actuator 105 is screwed into shell 112 to be inserted into one of the spaces 107 between adjacent ball bearings 120. Locking occurs since ball bearings 120 are substantially unable to move due to the close packing of the ball bearings and their abutment against edges 103a.

In other embodiments, the ball bearing can be disposed in other arrangements over the surface of the rounded member, for example, in linear grooves. To facilitate assembly of the joint of FIG. 11A, the rounded member can be magnetized to attract the ball bearings (made of steel).

Ball bearings 120 can be closely packed over the entire surface of a central ball by spacing the shell from the surface of the ball, to accommodate the ball bearings therebetween, and by placing a slideable plate covering (not shown) over opening 114 to prevent the ball bearings from passing therethrough. In other embodiments, ball bearings can be disposed in other arrangements over the surface of the ball.

In another embodiment of a rounded member, shown in FIG. 11C dimples 125 are formed in the surface of recessed area 103 to accept ball bearings 120. To prevent ball bearings 120 from moving out of position a close fitting shell as shown in FIG. 11A is provided. When ball bearings 120 are positioned in dimples and the shell is close fitting thereover so that ball bearings cannot move out of dimples, the edges 103a' of a recess 103' need not closely conform to the perimeter shape of the ball bearing arrangement.

Figure 11D:
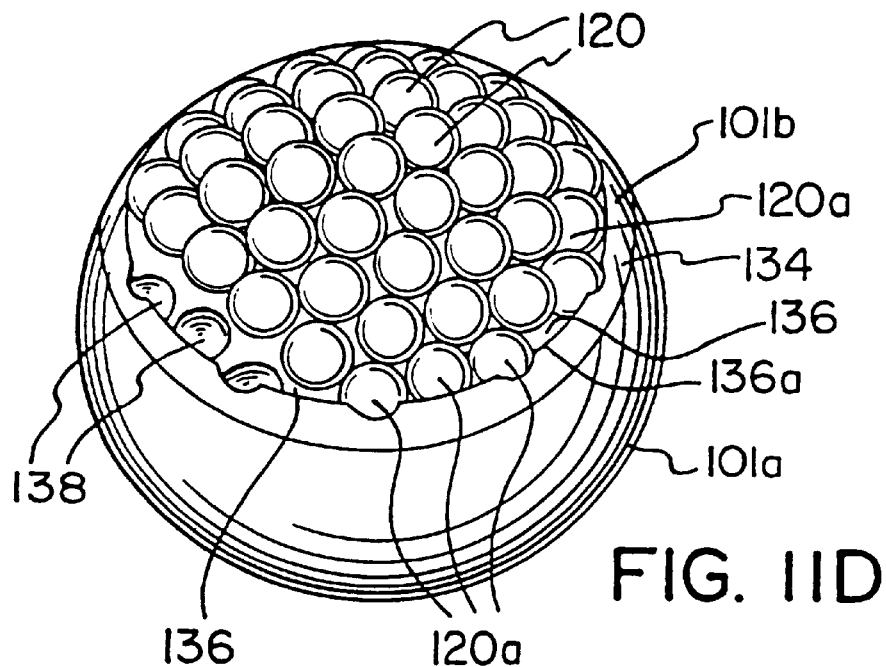
FIG. 11D a perspective view, partly cut away of an alternate rounded member useful in the joint of FIG. 11A.

In another embodiment shown in FIG. 11D, the rounded member is formed in two sections: a main section 101a and a ball bearing retaining section 101b. Ball bearing retaining section 101b is formed to hold ball bearings 120 in a selected pattern. Section 101b is attached to section 101a by mating parts or any other suitable attachment means and includes edge 134 which continues the surface curvature of the section 101a and a recess 136, defined by edges 136a, which accommodates and maintains the positioning of ball bearings 120. Cavities 138 are formed in recess 136 to accept and precisely position ball bearings 120a. Preferably section 101a is formed of a light weight material such as aluminum and section 101b is formed of durable material such as hardened steel.

Figure 12:
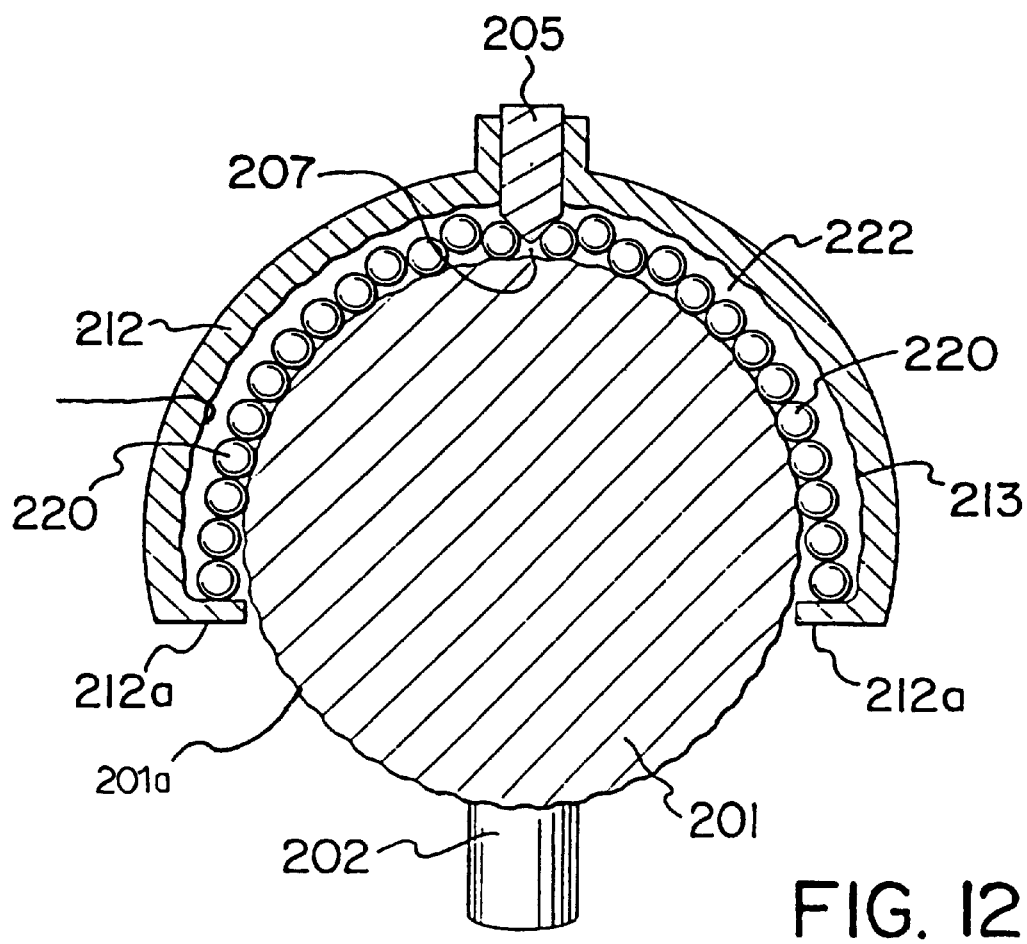
FIG. 12 is a sectional view through another embodiment of a ball joint according to the present invention.

In yet another embodiment, as shown in FIG. 12, the ball joint includes a central ball 201 and a shank 202 attached thereto. A shell 212 is disposed around ball 201. Shell 212 is formed at its edges 212a to fit closely over ball 201. Shell 212 is further formed such that the inner surface 213 of shell 212 is spaced from the surface of ball 201 to define a cavity 222 sized to accommodate a single layer of closely packed ball bearings 220. There can be any number of ball bearings disposed in the cavity. For example, the minimum possible number of ball bearings in the cavity is two and the cavity is sized as to be fully packed by the two ball bearings. The volume of the cavity is selected to provide close packing of the ball bearings. The distance between the surface of ball 201 and the surface of cavity 222 is selected to be greater than the diameter of the ball bearings but less than twice that diameter. An actuator 205 is engaged by shell 212 is extendable into cavity 222.

Shell 212 and ball bearings 220 are free to move over the surface of ball 201 when actuator 205 is retracted. When actuator 205 is moved into cavity and forced into a space 207 between an arrangement of ball bearings 220, the ball bearings are forced apart and move relative to one another to accommodate the actuator. This causes the ball bearings to be pushed into frictional engagement with each other, the inner surface 213 of shell and the surface of the ball 201. Thus, the force of the actuator moving into. the cavity to displace the ball bearings is transmitted through the arrangement of ball bearings to cause engagement between the shell and the ball over the entire arrangement of ball bearings. To cause locking of the orientation of the ball joint, the volume of the cavity, the number of ball bearings and the volume of the actuator tip are selected to ensure that the ball bearings are substantially at maximum density per volume of the cavity when the actuator is in locking position within the cavity.

To enhance the engagement between the ball bearings, shell and ball, one or both of the ball surface 201a and the inner shell surface 213a can be dimpled (as shown), knurled or otherwise-roughened.

The actuator of the ball joint of the present invention can be moved between a retracted position and a locked position within a concavity or space between engaging surfaces by any suitable means such as by screwing where thread is provided between the actuator and the shell, as shown hereinbefore.

Figure 13A:
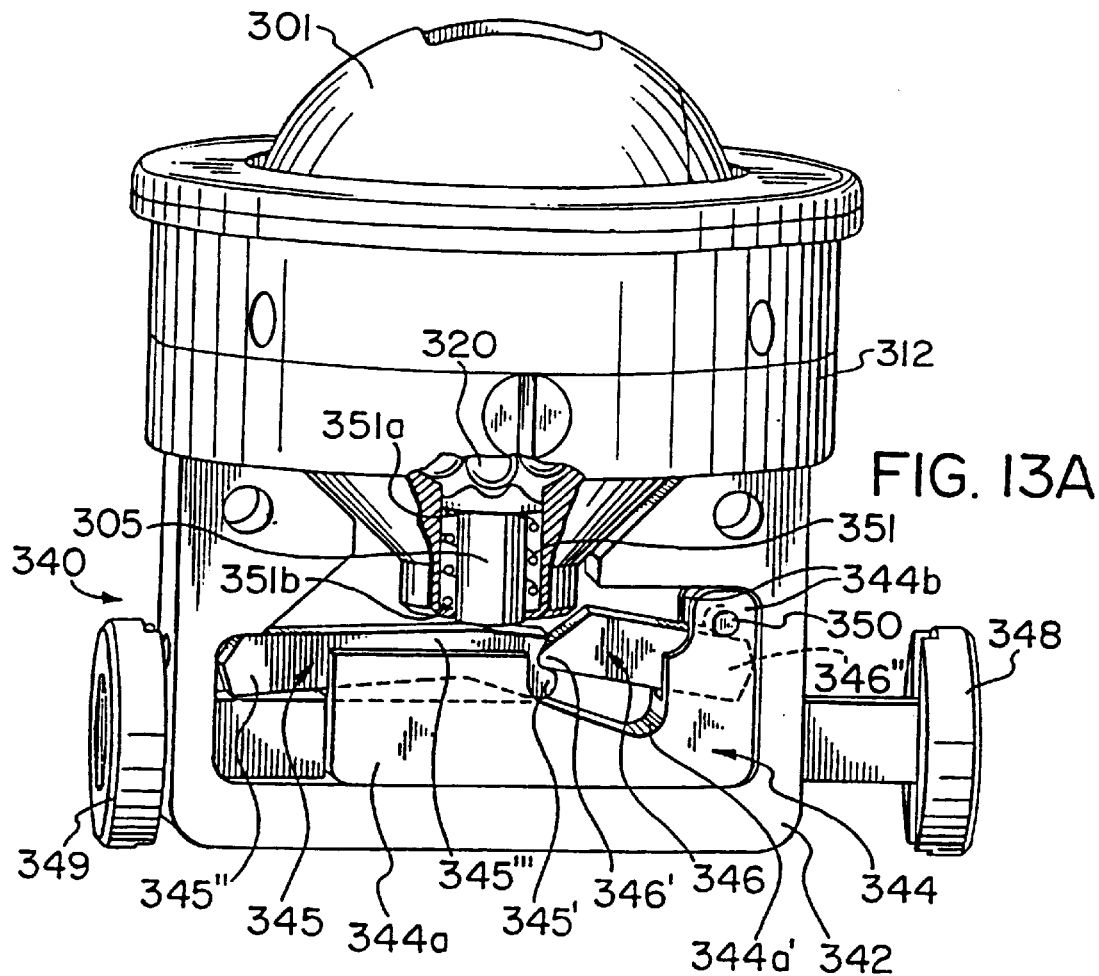
FIG. 13A is a perspective view of a ball joint according to the present invention with the housing removed to reveal the actuator drive mechanism.
Figure 13B:
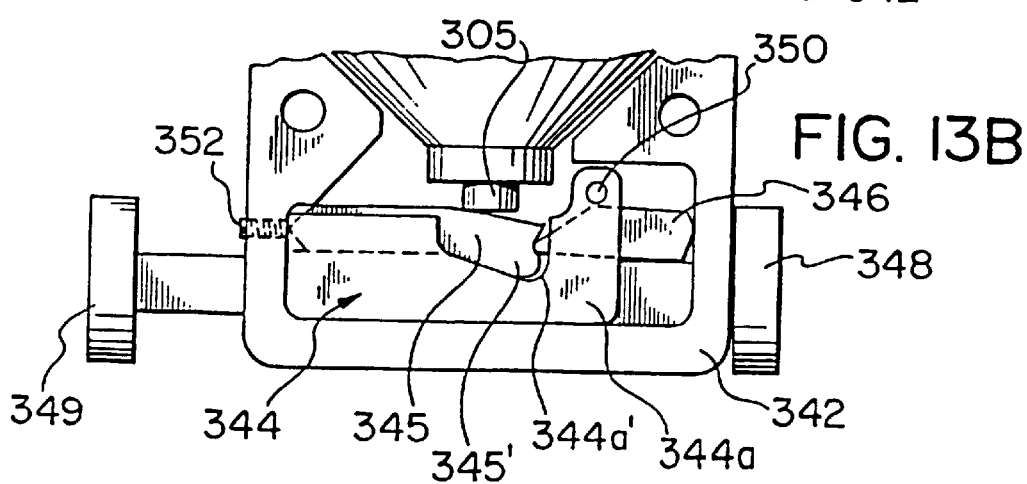
FIG. 13B is a perspective view of the actuator drive mechanism in the disengaged position where the actuator is retracted.

Referring to FIGS. 13A and 13B one means is shown wherein the movement of actuator 305 is driven by a mechanism 340. Mechanism 340 includes a housing 342 in engagement with the shell 312 of the ball joint which accommodates a carriage 344 and interlocking parts 345, 346. Switch buttons 348, 349 are rigidly connected to carriage 344 and extend out through housing 342. Carriage 344 includes a base 344a and walls 344b. Interlocking parts 345, 346 are maintained between walls 344b (Parts 345, 346 are shown in phantom where they are positioned out of view to facilitate understanding). Stop 350 extends between walls 344b above part 346. Base 344a is formed with a central recessed portion 344a' sized to accommodate end 345' of part 345. Recessed portion 344a' has a sloped side along which part 345 can slide. Part 345 is tapered at its central portion 345'". Parts 345 and 346 are connected by interlocking at their ends 345', 346' by a protrusion on part 346 extending into a groove on part 345. Parts 345 and 346 are pivotally moveable about the interlocking connection from a raised position as shown in FIG. 12A to a collapsed position as shown in FIG. 12B. Opposite ends 345", 346" of the parts abut against housing 342. Part 345 contacts actuator 305.

Mechanism 340 is operated to move actuator 205 by applying force to buttons 348 and 349 in turn. When actuator 305 is in the retracted position, as shown in FIG. 12B, parts 345, 346 are in the collapsed position with end 345' of part 345 resting in recessed portion 344a' and is interlocked with end 346' of part 346. When force is applied to button 349, carriage 344 is moved along housing 342 until it abuts against the side wall of housing 342, as shown in FIG. 12A. Such movement of carriage 344 causes end 345' of part 345 to ride up the ramp side of recessed portion 344a'. This also causes part 345 to move up and drive actuator into locking engagement with ball bearing 320 retained on ball 301. Ball 301 is a part of a ball joint as shown in FIG. 10A, and is thereby locked in position. To disengage actuator 305 from ball 301, force is applied to button 348 and carriage 344 is thereby moved back along housing 342 to assume a position as shown in FIG. 12B. Such movement of carriage 344 causes stop 350 to move over the upper surface of part 346 and force it down against base 344a. This, in turn, causes part 345 to be forced down into recessed portion 344a' and away from actuator 305. Actuator 305 is now free to move out of locking position with ball bearing 320. A spring 351 is positioned about actuator 305 to act between area 351a on the actuator and area 351b on the actuator housing to prevent the actuator from falling fully out of engagement with ball bearings so that the ball bearings do not drop into actuator housing. A cover (not shown) is provided over the open sides of housing 342, when in use. A tension screw 352 can be provided through housing 342 to allow for adjustment in the tension between interlocking parts 345, 346.

The switch mechanism can be used in a prosthetic joint, such as a wrist joint. This mechanism can be actuated through a rubber sleeve, such as is commonly worn over a prosthetic limb, thereby avoiding interfering with the natural appearance of the sleeve. The switch is easy to produce because hinges are not required and many parts can be produced by extrusion and stamping processes. In addition, the materials selected for production of the parts can be selected independently with consideration as to the weight and durability required. As an example, in a prosthetic joint, the parts 345, 346, carriage 344 and actuator 305 may be formed of stainless steel to enhance their resistance to wear, while housing 342, and buttons 348, 349 can be formed of light weight materials such as polymers. Repair of the present joint is facilitated since parts 345, 346, housing 342 and carriage 344 can be replaced independently.

Figure 14A:
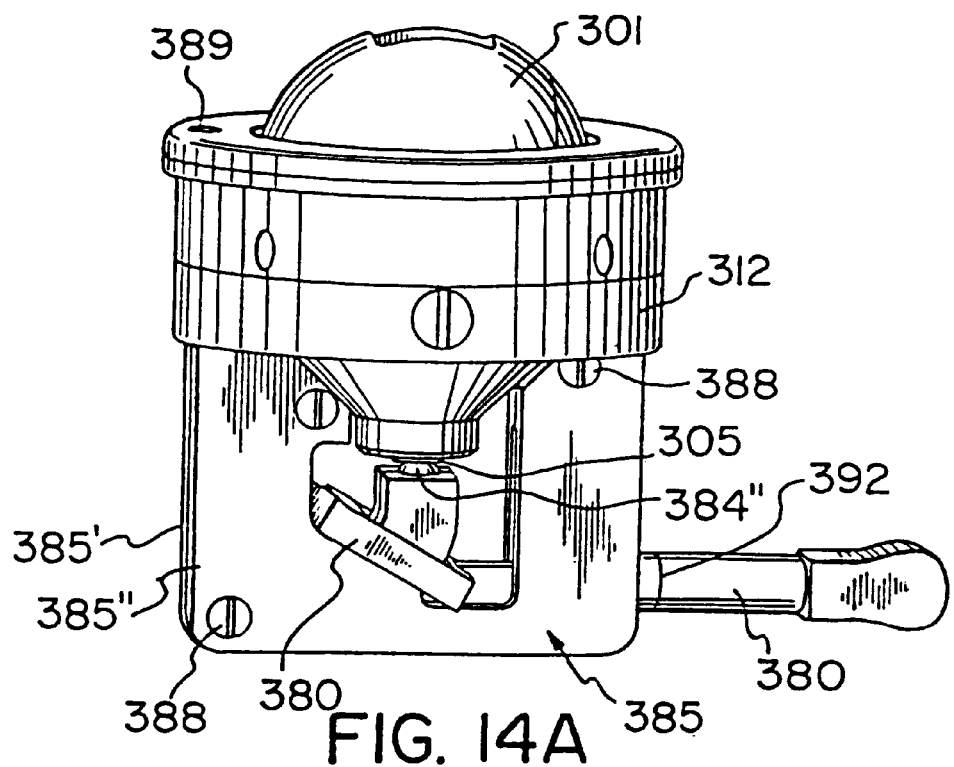
FIG. 14A is a perspective view of another actuator drive mechanism useful in the present invention.
Figure 14B:
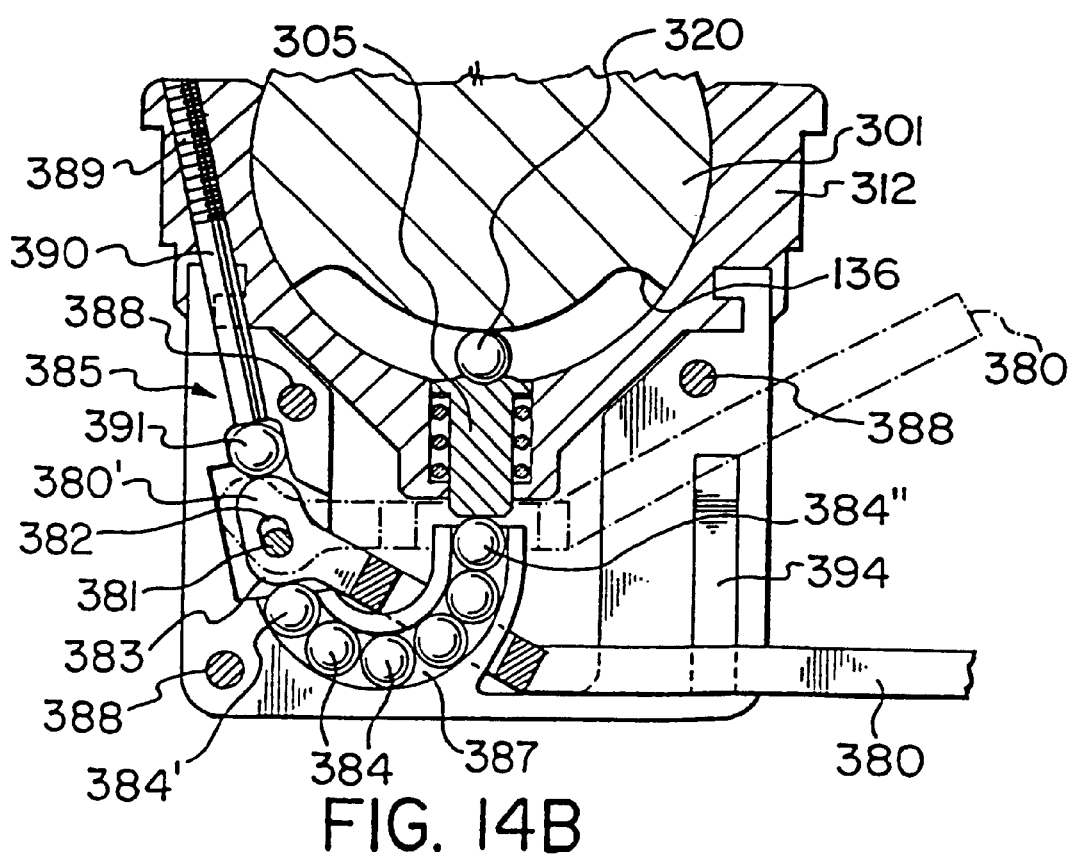
FIG. 14B is an elevation, partly in section of the mechanism of FIG. 14A.

Referring to FIGS. 14A and 14B another actuator switch mechanism useful in driving the actuator of a ball joint is shown. The mechanism includes a lever 380 attached by pin 381 through an aperture 382 in lever end 380'. End 380' is formed with an enlarged portion 383. End 380 is secured by pin 381 such that portion 383 is positioned in communication with a first ball bearing 384' of a string of ball bearings 384. Each ball bearing in string 384 is positioned in contact with its adjacent ball bearings. The last ball bearing 384" is in contact with actuator 305 of a ball joint. A housing 385 holds the parts together and, in particular, retains pin 381 and has formed therein a channel 387 for accommodating the ball bearings in line.

In use lever 380 is pivotally moveable on pin 381 between a first position and a second position, shown in phantom in FIG. 14B. When lever 380 is moved into the first position, enlarged portion 383 presses onto ball bearing 384' and drives bearings 384 through channel 387, thereby causing ball bearing 384" to drive actuator 305 toward the rounded member 301 of the ball joint and into locking engagement with one, as shown, or more ball bearings 320 retained in a recess 136 on rounded member 301. (It is to be understood that a recess sized as shown in the Figure would accommodate a plurality of tightly packed ball bearings when is use. However, only one ball bearing has been shown for clarity.) When lever 380 is moved to the second position, the pressure on the bearings is removed and the actuator is removed from locking engagement with ball bearing 320.

Preferably, housing 385 is formed as two halves 385', 385" to facilitate assembly. Halves 385', 385" are joined by screws 388. Housing 385 is attached to shell 312 of ball joint. In FIG. 14B one half of the housing has been removed to expose the structures within the housing.

To provide for adjustment of locking pressure, an adjusting screw 389 and extension rod 390 are mounted with rod in communication with end 380' of lever 380. Aperture 382 is elongate to permit adjustments in the positioning of lever 380. Preferably a ball bearing 391 is provided to ease rotational movement of end 380' past rod 390.

In a preferred embodiment, the length of lever 380 is adjustable by insertion of spacers at connection 392. Preferably also, an elastomeric strip 394 is affixed to housing adjacent lever 380 to provide some resistance to the movement of the lever.

Figure 15C:
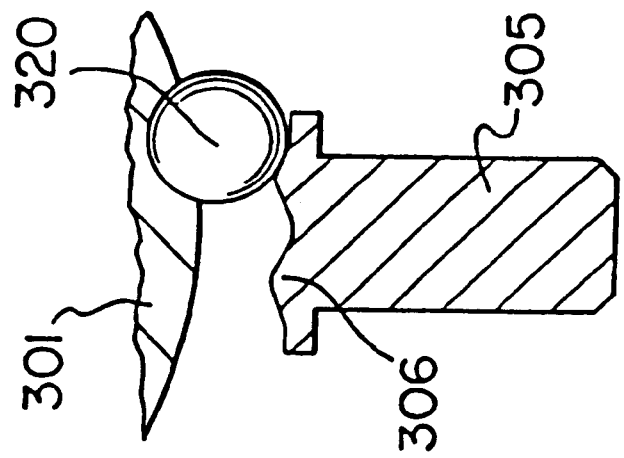
FIGS. 15A to 15C is a series of schematic views showing actuator/ball bearing engagement.
Figure 15B:
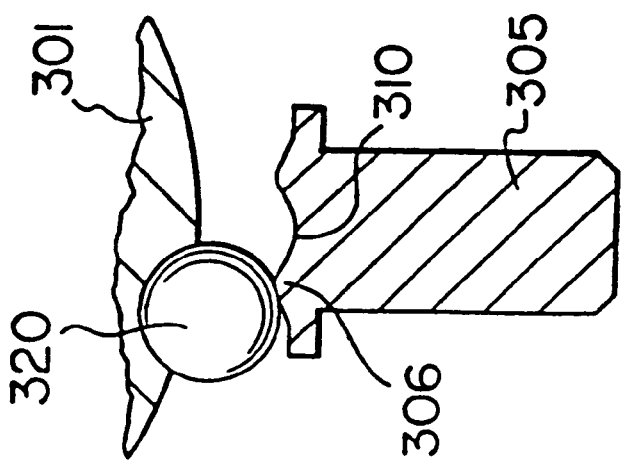
Figure 15A:
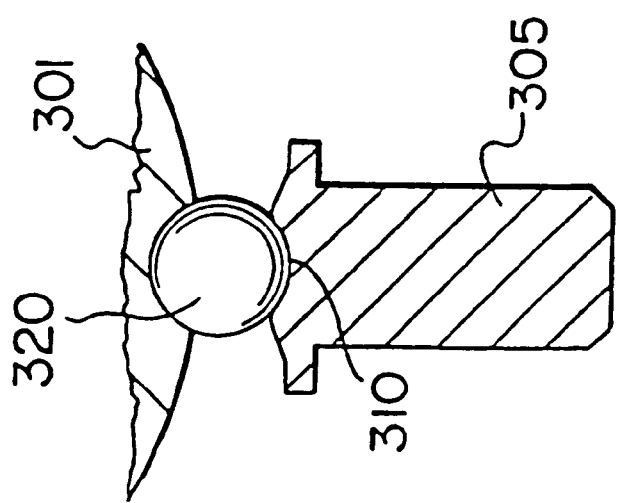

It is preferred that the actuator be lockable with the engaging surfaces of the ball joint at any site on the rounded member. In this arrangement, the actuator must be able to lock at different penetrations as shown in FIG. 15A to 15C. When the actuator locks with, for example, an engaging surface formed as a ball bearing, actuator 305 can be required (a) as shown in FIG. 15A, to lock with a ball bearing 320 disposed in its tip indentation 310 or (b) as shown in FIG. 15B, to lock with a ball bearing 320 near the outer end of the tip 306 or (c) as shown in FIG. 15B, to lock with a ball bearing 320 near the base of the tip 306. To lock in these ways the actuator must be adjustable to penetrate into the shell the desired distance and rigidly lock in that position. For example, in a prosthetic wrist joint having a ball joint formed by ball bearings, the penetration difference between a locking as shown in FIG. 15A and a locking as shown in FIG. 15C can be about 8 one thousands of an inch.

The actuator drive mechanism can be adjustable by any suitable means to have variable penetration into the shell such as, for example, by turning of an adjustment screw 389 as shown in FIG. 14B. Preferably, the actuator drive mechanism is selected to be self-adjusting to accommodate variable penetration depths and to lock-with the engaging surface it first comes into contact with regardless of the actuator depth of penetration into the shell.

One embodiment of a self-adjusting actuator drive mechanism is shown in FIGS. 16A and 16B. The mechanism includes an actuator pin lever 410 pivotally connected by pin 411 to ball joint shell 412 to be moveable into contact with actuator pin 405. Lever 410 is pivotally connected at 415 to operating lever 416. A rigid part 417 is pivotally connected at its first end by pin 418 to operating lever 416 and pivotally connected at its opposite end by pin 419 to a locking wedge system 420. Locking wedge system 420 includes a first wedge 421 to which part 418 is pivotally attached, a second wedge 422 and a spacer plate 424 disposed therebetween. Wedges 420, 422 and spacer plate 424 are housed in a cavity 426 defined by a rear wall 427, top and bottom walls 429a and side walls 429b (only one can be seen, the other being removed to allow a view into the cavity). Top and bottom walls 429a are spaced a distance from each other which is selected to be just less than the measured thickness of wedge 421, spacer 424 and wedge 422 in stacked arrangement so that the stacked arrangement can be wedged between walls 429a. Grooves 430 are formed on opposing side walls 429b and accommodate tabs 431 on plate 424. The length of grooves 430 are selected to limit the movement of plate 424 along the cavity by abutment of tabs 431 on edges of grooves 430. Wall 427 simply prevent the parts from falling out of the cavity. A spring 433 is attached between lever 410 and wedge 422. Preferably, spring 433 is attached to a spring tension adjustment screw 434 is threaded into an aperture in wedge 422. By the adjustment of screw 434, the tension in spring 433 and thereby the locking tension of the mechanism can be adjusted.

When not wedged between walls 429a, wedges 421, 422 and plate 424 are moveable longitudinally along the cavity, except as limited by the connections to spring 433, part 417 and grooves 430. In the unlocked position as shown in FIG. 16A, wedge 422 is positioned within cavity 426 according to the pivotal position of lever 410 which moves spring 430. Wedge 421 is positioned loosely in cavity above spacer plate 424. To lock the actuator 405 to a ball bearing 420 on a ball joint rounded member 401, lever 416 is pivoted about 415 which will move lever 410 pivotally into contact with actuator 405. Actuator 405 will move upwardly by the force of lever until it is in contact with ball bearing 420. The movement of the lever 410 is translated to wedge 422 by spring 433 and screw 434. Wedge 422 will move along the cavity as lever 410 moves, when lever 410 stops, wedge 422 will also stop and its position will be fixed until lever 410 is again moved. Pivotal movement of lever 416 will at the same time, though part 417, drive wedge 421 toward wall 427 in cavity 426, as shown by arrow W. Wedge 421 moves over plate 424, until the arrangement of wedges 421, 422 and plate 424 is wedged between walls 429a. Once such wedging has occurred, lever 416 is further pivoted until pivotal connection 418 is over-centered. The actuator tip will then be locked to the ball bearing. To unlock the actuator tip from the ball bearing, the lever 416 is pivoted back to pull wedge 421 out of wedging position in cavity 421. The ball joint can then be moved into another angular orientation. Preferably, lever 410 is slidably attached to actuator 405 so that movement of the actuator is directly translated to wedge 422 and so that lever 416 will pivot through a more limited range.

Figure 17A:
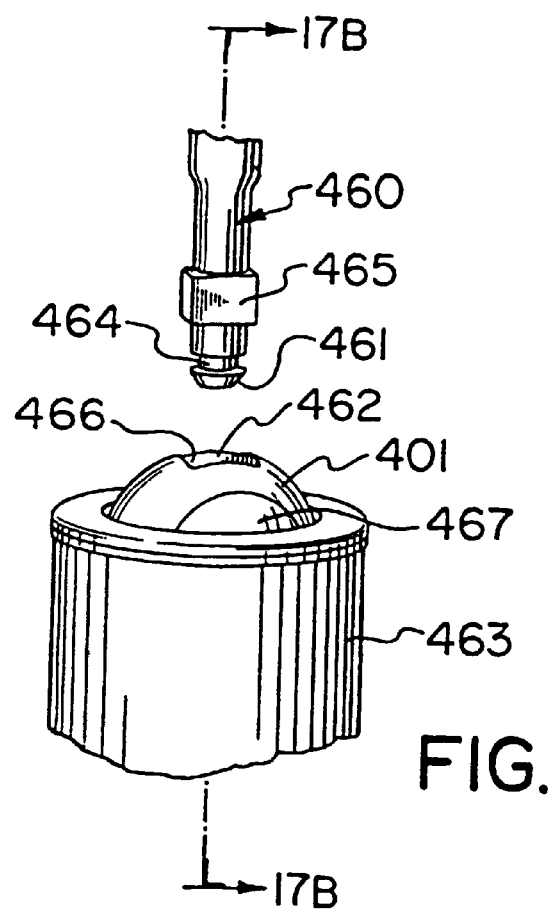
FIG. 17A is a perspective view of a prosthetic terminal device locking mechanism according to the present invention, with the stem aligned for entry into the bore.
Figure 17B:
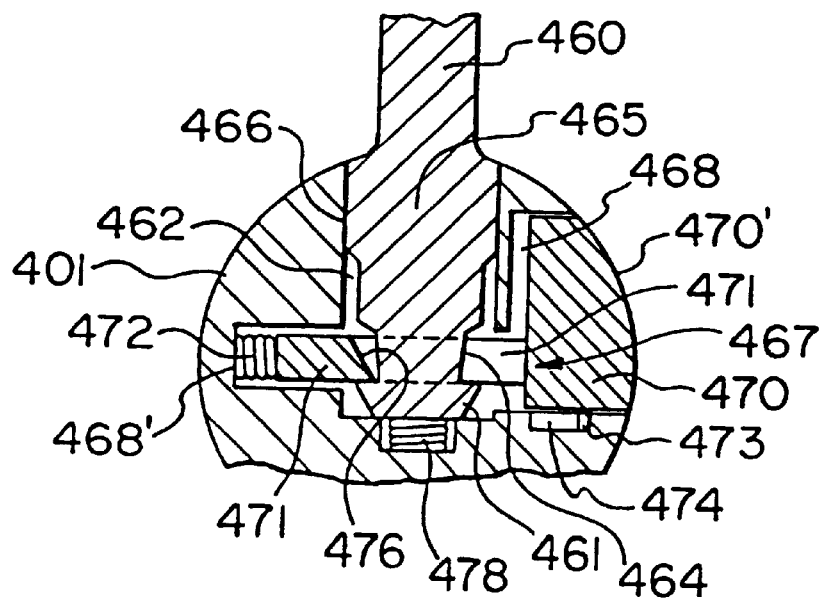
FIG. 17B is a sectional view along line 17B—17B of FIG. 17A with the stem in the bore.

Referring to FIGS. 17A and 17B, a locking assembly is shown. The locking assembly is of use in various fields including with a ball joint. The locking assembly includes a stem 460 and a bore 462. (FIG. 17A shows stem 460 aligned for entry into bore 462, while FIG. 17B shows stem 460 engaged in bore 462.) In the embodiment shown, bore 462 is formed in a ball 401 of a ball joint.

Stem 460 is formed to have a chamfered tip 461, an annular groove 464 and an enlarged portion 465 formed as a square in cross-section. The walls 466 defining the opening of bore 462 likewise form a square to mate with portion 465 and prevent rotation of the stem within the bore. A push button 467 is exposed on the outer portion of ball 401 to provide for actuation of the locking assembly. Push button 467 is shown only partly exposed in FIG. 17A. Ball 401 can be rotated to enhance access to button. 467.

Button 467 is normally flush with ball 401 to allow proper functioning of the ball joint. Button 467 is disposed in a cavity 468 formed in the ball in communication with bore 462. Button 467 includes a body portion 470 having an exposed surface 470' open to the ball surface. An elongate portion 471 extends from the back of body 470. A spring 472 acts between a wall 468' of cavity 468 and elongate portion 471 to bias button 467 outwardly. To prevent button 467 from being forced out of cavity 468 by the action of spring 472, a pin 473 is formed on or engaged to the button which abuts against the walls of a hole 474 formed in a wall of the cavity. Elongate portion 471 has formed therethrough an aperture 475 which, when the button is positioned in cavity 468, aligns with bore 462 of ball 401. A wall 476 defining the aperture is chamfered. When button 467 is biased outwardly wall 476 extends into bore 462.

To lock stem 460 into bore 462, stem 460 is inserted into bore 462 and turned such that portion 465 fits into opening 466. The stem will then drop onto elongate portion 471 of button 467. Force can be applied parallel to the central axis of the stem, as shown by arrow a, to drive the chamfered surfaces 461 and 476 past one another and thereby to drive the button against spring 472. This allows the stem to move past the elongate portion of the button. As the stem moves into the bore, elongate portion 471 will be biased into groove 464. Elongate portion 471 will then prevent stem 460 from being removed from bore 462 by acting against the walls of groove 464.

To remove stem 460 from bore 462, force is applied to button 467 to move elongate portion 471 out of engagement with the walls of groove 464. Preferably, the button can be actuated by a simple application of force along one axis to facilitate removal of the terminal device.

In a preferred embodiment as shown, a spring 478 is provided at the base of bore 462 which is compressed by the tip of stem 460 when it is completely inserted into bore 462. Spring 478 will bias stem 462 outwardly when button is pressed.

Figure 18A:
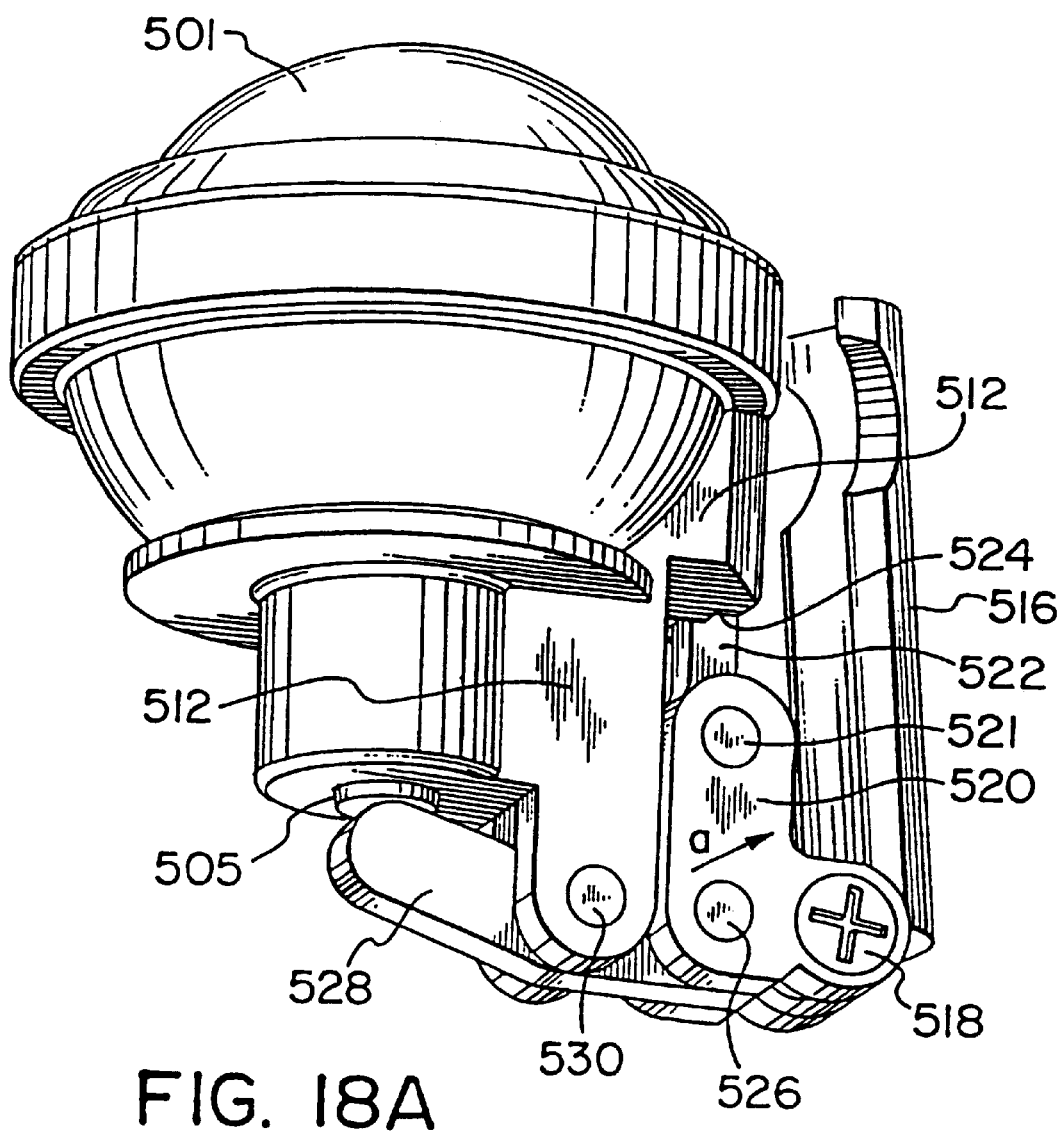
FIG. 18A is a perspective view of a ball joint according to the present invention.

Referring to FIGS. 18A and 18B, a ball joint assembly is shown having an actuator drive mechanism including a lever 516 rigidly attached by screw 518 to a link 520. Link 520 is pivotally connected by pin 521 to a part 522 which is slidably engaged in a groove 524 in ball joint shell 512. Part 522 can slide in groove 524 until its end 522a abuts against stop wall 525 formed in shell 512. Link 520 is further pivotally connected by pin 526 to actuator lever 528 which pivots about fulcrum 530 into contact with actuator 505.

Mechanism works to drive actuator 505 into shell and thereby into engagement with an engaging surface such as a protrusion on a ball 501. In the locked position as shown in FIG. 18A, lever 528 is locked into contact with actuator 505. Lever 528 is locked in this position by action of link 520 and part 522 which are in tension by over-centering at 521 and abutting of parts 520 and 522 between pin 526 and stop 525. To release actuator 505 from engagement with at least one protrusion 504, lever 516 is pulled outwardly from shell 512. This causes pivotal movement around pin 521 and if suitable force is applied to lever 516, to overcome the tension between the parts 520 and 522, pivotal movement will occur around pin 526 and fulcrum 530 so that the link moves in the direction shown by arrow a. This causes lever 528 to move away from actuator 505. A set screw 531 can be provided to act against part 522 to allow adjustment in the locking tension.

FIG. 18B shows how parts generally as described herein can be assembled to construct a ball joint according to the present invention. The actuator drive mechanism as described in FIG. 18A is assembled by connecting parts 516, 520, 522 and 528 by securing screw 518 and pins 521 and 526 into appropriate holes, as shown. Part 522 is mounted onto shell 512 by insertion of a press fit pin 540 into aperture 541 and insertion of pin into groove 524. Lever 528 is then secured to shell 512 by fulcrum pin indicated as 530 into an appropriate hole 543 formed in the shell.

A rounded member 501, generally according to FIG. 17A, is assembled by inserting spring 472 and button 467 into cavity 468 and securing the assembly therein by inserting pin 473 between the button and hole 474. Spring 478 is inserted into bore 462'. Bore 462' is formed to accept and lock with a stem 460', as shown, having a groove 464 and a shaped portion 465'. Stem 460' has a threaded end 545 for connection with a selected part.

Spring 551 and actuator 505 are inserted into shell 512 and rounded member 501 in assembled form is inserted thereover. Shell ring 512a is screwed onto shell 512 to hold rounded member 501 therein.

This assembly procedure can be carried out in any logical sequence.

It will be apparent that many changes may be made to the illustrative embodiments, while falling within the scope of the invention and it is intended that all such changes be covered by the claims appended hereto.

What is claimed is:

1. An angularly adjustable, releasably lockable joint mechanism for rigidly joining first and second parts together at a selected orientation, said mechanism comprising a rounded member and a socket, the rounded member is rotatable within the socket, and at least one disengageable actuator acting between the rounded member and the socket, having a tip and means for advancing the tip toward the rounded member and locking the socket and rounded member together; said rounded member having two sections which define a recessed area in which spherical members are located in said recessed area, said two sections intersecting to define an intersection, said intersection is located adjacent to said spherical members and said intersection engages several of said spherical members and maintains said spherical members closely packed in position in said recessed area.

2. Joint mechanism according to "claim 1" the actuator is driven by pushable means to advance and retract the tip.

3. Joint mechanism according to "claim 1" further including a means for adjusting a locking tension between said actuator and said rounded member.

4. Joint mechanism according to claim 1 the actuator is driven by a means for adjustably selecting a distance the actuator extends into the socket when fully extended.

5. Joint mechanism according to claim 1 the actuator is driven by a means for adjustably locking the actuator into position in the socket.

6. Joint mechanism according to claim 1 wherein the actuator is driven by a means for adjustably locking the actuator in contact with an engaging surface.

7. The joint mechanism as defined in claim 1 wherein said intersection is undulating in shape.

8. The joint mechanism as defined in claim 1 further including a continuation portion on one of said sections having recesses defined therein and the recesses are located to accommodate some of said spherical members.

9. The joint mechanism as defined in claim 1 further including pockets in said rounded members each accommodates one of said spherical member.

* * * * *